United States Patent
Mino et al.

(10) Patent No.: US 11,439,301 B2
(45) Date of Patent: Sep. 13, 2022

(54) OPHTHALMOLOGIC INFORMATION PROCESSING APPARATUS, OPHTHALMOLOGIC APPARATUS AND OPHTHALMOLOGIC INFORMATION PROCESSING METHOD

(71) Applicant: TOPCON CORPORATION, Tokyo (JP)

(72) Inventors: Toshihiro Mino, Saitama (JP); Jonathan Liu, Tokyo (JP)

(73) Assignee: TOPCON CORPORATION, Tokyo (JP)

( * ) Notice: Subject to any disclaimer, the term of this patent is extended or adjusted under 35 U.S.C. 154(b) by 608 days.

(21) Appl. No.: 16/408,483

(22) Filed: May 10, 2019

(65) Prior Publication Data
US 2020/0221947 A1   Jul. 16, 2020

Related U.S. Application Data

(60) Provisional application No. 62/793,044, filed on Jan. 16, 2019.

(51) Int. Cl.
*A61B 3/10* (2006.01)
*A61B 3/00* (2006.01)
(Continued)

(52) U.S. Cl.
CPC .......... *A61B 3/102* (2013.01); *A61B 3/0025* (2013.01); *A61B 3/103* (2013.01); *G06T 7/0012* (2013.01);
(Continued)

(58) Field of Classification Search
CPC ....... A61B 3/102; A61B 3/0025; A61B 3/103; A61B 3/14; G06T 7/0012;
(Continued)

(56) References Cited

U.S. PATENT DOCUMENTS 8,085,408 B2   12/2011   Everett et al.
8,442,286 B2   5/2013    Imamura et al.
(Continued)

FOREIGN PATENT DOCUMENTS

EP   2 404 545 A2   1/2012
EP   3 075 303 A1   10/2016
(Continued)

OTHER PUBLICATIONS

Extended European Search Report dated Jun. 9, 2020 in European Patent Application No. 19219988.3, 7 pages.
(Continued)

*Primary Examiner* — Mohammed A Hasan
(74) *Attorney, Agent, or Firm* — Xsensus LLP

(57) ABSTRACT

An ophthalmologic information processing apparatus includes an acquisition unit, a tissue specifying unit, and a specifying unit. The acquisition unit is configured to acquire a tomographic image of a subject's eye. The tissue specifying unit is configured to acquire first shape data representing shape of a tissue of the subject's eye by performing segmentation processing on each of a plurality of tomographic images acquired by the acquisition unit. The specifying unit is configured to obtain second shape data representing shape of the tissue based on the plurality of first shape data acquired by the tissue specifying unit.

28 Claims, 8 Drawing Sheets

(51) Int. Cl.
*A61B 3/103* (2006.01)
*G06T 7/00* (2017.01)
*G16H 30/40* (2018.01)
*A61B 3/14* (2006.01)

(52) U.S. Cl.
CPC ....... *A61B 3/14* (2013.01); *G06T 2207/10101* (2013.01); *G06T 2207/30041* (2013.01); *G16H 30/40* (2018.01)

(58) Field of Classification Search
CPC . G06T 2207/10101; G06T 2207/30041; G06T 7/11; G06T 7/136; G16H 30/40
USPC .......................................................... 351/206
See application file for complete search history.

(56) References Cited

U.S. PATENT DOCUMENTS

| | | | |
|---|---|---|---|
| 8,517,537 | B2 | 8/2013 | Suehira et al. |
| 8,684,528 | B2 | 4/2014 | Fujimura et al. |
| 8,712,505 | B2 | 4/2014 | Ishikawa et al. |
| 9,025,844 | B2 | 5/2015 | Iwase et al. |
| 9,149,181 | B2 | 10/2015 | Matsumoto et al. |
| 9,706,914 | B2 | 7/2017 | Bagherinia et al. |
| 10,537,243 | B2 | 1/2020 | Ikegami |
| 2008/0100612 | A1* | 5/2008 | Dastmalchi .......... A61B 5/7445 345/418 |
| 2010/0189334 | A1 | 7/2010 | Tomidokoro et al. |
| 2012/0002164 | A1 | 1/2012 | Yamamoto et al. |
| 2012/0069298 | A1* | 3/2012 | Ng .......................... A61B 3/18 351/206 |
| 2013/0010259 | A1* | 1/2013 | Carnevale ............. A61B 3/102 351/206 |
| 2013/0242259 | A1 | 9/2013 | Hacker et al. |
| 2015/0085252 | A1 | 3/2015 | Fujimura et al. |
| 2015/0366450 | A1 | 12/2015 | Ren et al. |
| 2016/0331224 | A1 | 11/2016 | Uji et al. |
| 2016/0345822 | A1 | 12/2016 | Fujimura et al. |
| 2017/0127936 | A1* | 5/2017 | Iwase ................... A61B 3/0025 |
| 2017/0135568 | A1 | 5/2017 | Charles |
| 2017/0181620 | A1 | 6/2017 | Andrews et al. |
| 2017/0245756 | A1 | 8/2017 | Hayashi et al. |
| 2018/0192870 | A1 | 7/2018 | Inao et al. |
| 2018/0289257 | A1 | 10/2018 | Ikegami |

FOREIGN PATENT DOCUMENTS

| | | |
|---|---|---|
| JP | 2013-248376 A | 12/2013 |
| JP | 2016-77774 A | 5/2016 |
| JP | 2018-175258 A | 11/2018 |

OTHER PUBLICATIONS

Office Action dated Sep. 17, 2020, in corresponding U.S. Appl. No. 16/377,263, 27 pages.
Extended European Search Report dated Jun. 9, 2020 in European Patent Application No. 19219987.5, 8 pages.
Extended European Search Report dated Jun. 9, 2020 in European Patent Application No. 19219979.2, 8 pages.
U.S. Office Action dated Apr. 13, 2021, in corresponding U.S. Appl. No. 16/412,433.
Office Action dated Mar. 25, 2021, in corresponding U.S. Appl. No. 16/377,263, 20 pages.
Verkicharla et al., "Eye shape and retinal shape, and their relation to peripheral refraction", The Journal of the College of Optometrists, Ophthalmic & Physiological Optics 2012, vol. 32, pp. 184-199.
Smith et al., "Relative peripheral hyperopic defocus alters central refractive development in infant monkeys", Sep. 2009, vol. 49, No. 19, pp. 2386-2392.
Office Action dated May 25, 2022, in corresponding European patent Application No. 19219988.3, 8 pages.

* cited by examiner

OPHTHALMOLOGIC INFORMATION PROCESSING APPARATUS, OPHTHALMOLOGIC APPARATUS AND OPHTHALMOLOGIC INFORMATION PROCESSING METHOD

CROSS-REFERENCE TO RELATED APPLICATION

This application is based upon and claims the benefit of priority from U.S. Provisional Application No. 62/793,044, filed Jan. 16, 2019; the entire contents of which are incorporated herein by reference.

FIELD

Embodiments according to present invention described herein relate to an ophthalmologic information processing apparatus, an ophthalmologic apparatus, and an ophthalmologic information processing method.

BACKGROUND

In recent years, as one of the causes of myopia progress, a possibility that myopia may progress as the retina tries to extend to the back side due to the focal point of the peripheral visual field being on the back side (sclera side) of the retinal surface has been reported (for example, Earl L. Smith et al. "Relative peripheral hyperoptic defocus alters central refractive development in infant monkeys", Vision Research, September 2009, 49 (19), pp. 2386-2392).

In order to suppress such myopia progress, eyeglasses and contact lenses, which move the focal position of the central visual field to the near side (cornea side) by increasing the refractive power of the peripheral visual field, have been developed. Further, refractive surgeries such as the wavefront-guided LASIK, which is performed based on wavefront aberration measured in advance, are also performed. Therefore, in such high-performance refractive correction, measuring accurately the refractive power of the peripheral visual field is required.

In addition, some types of eyeball shape have been ascertained (for example, Pavan K Verkicharla et al. "Eye shape and retinal shape, and their relation to peripheral refraction", Ophthalmic & Physiological Optics, 32 (2012), pp. 184-199).

Such eyeball shapes also include types of shapes common to people with myopia and the like. It is considered effective to measure the change of the shape with myopia progress and to feed back the measurement result to ways to cope with the myopia progress.

SUMMARY

One aspect of some embodiments is an ophthalmologic information processing apparatus including: an acquisition unit configured to acquire a tomographic image of a subject's eye; a tissue specifying unit configured to acquire first shape data representing shape of a tissue of the subject's eye by performing segmentation processing on each of a plurality of tomographic images acquired by the acquisition unit; and a specifying unit configured to obtain second shape data representing shape of the tissue based on the plurality of first shape data acquired by the tissue specifying unit.

Another aspect of some embodiments is an ophthalmologic apparatus including the ophthalmologic information processing apparatus described above, wherein the acquisition unit includes an OCT unit configured to acquire the tomographic image of the subject's eye by performing optical coherence tomography.

Still another aspect of some embodiments is an ophthalmologic information processing method including: a tomographic image acquisition step that acquires a tomographic image of a subject's eye; a tissue specifying step that acquires first shape data representing shape of a tissue of the subject's eye by performing segmentation processing on each of a plurality of tomographic images acquired in the tomographic image acquisition step; and a specifying step that obtains second shape data representing shape of the tissue based on the plurality of first shape data acquired in the tissue specifying step.

DETAILED DESCRIPTION

Figure 1:
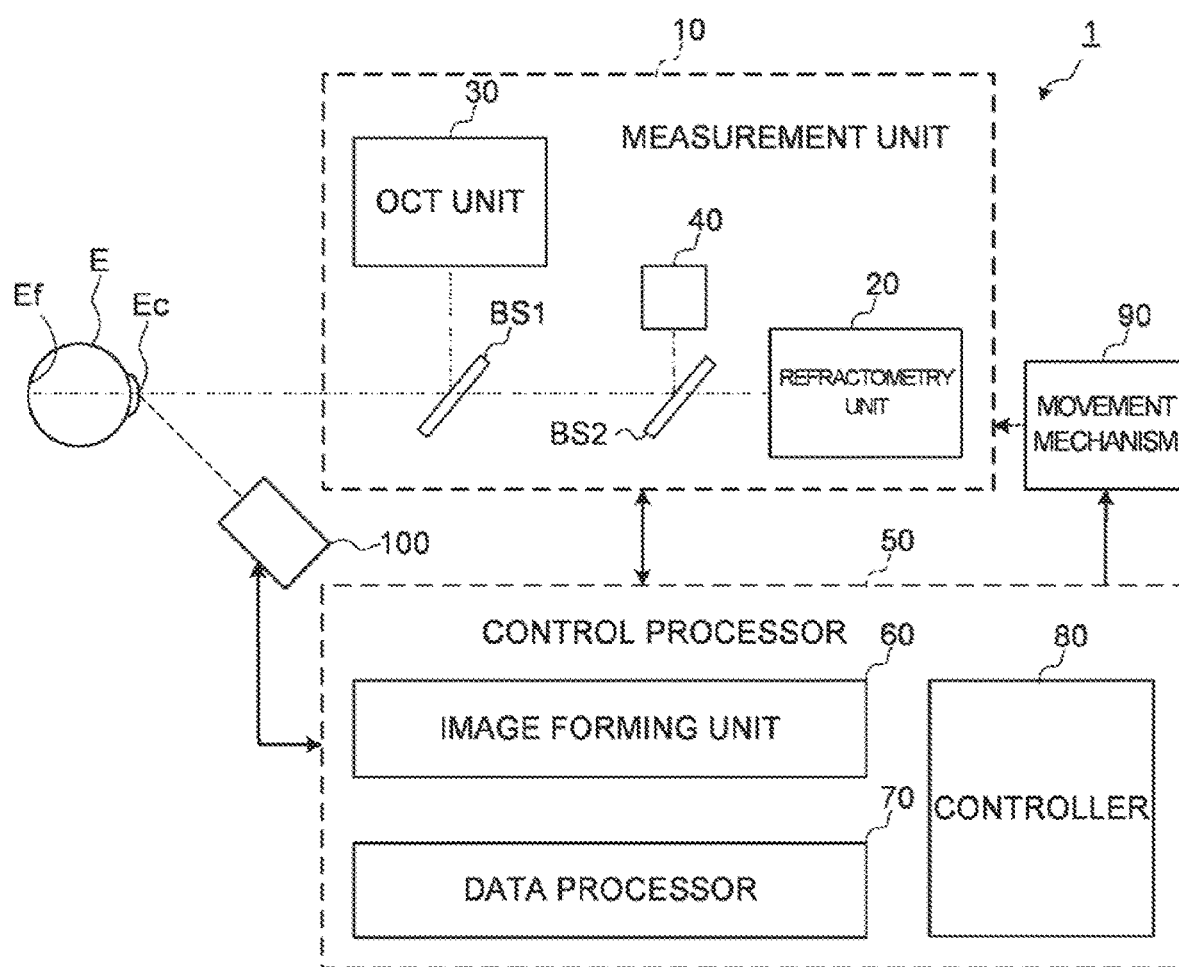
FIG. 1 is a schematic diagram illustrating an example of the configuration of an ophthalmologic apparatus according to the embodiments.

In general ophthalmologic apparatuses, a fixation target is projected onto a measurement optical axis. Thereby, the refractive power near the fovea of the retina is measured. In this case, taking into account the shape of the tissue in the fundus or the like (shape of the eyeball), it is possible to obtain the refractive power of the peripheral visual field from the refractive power of the vicinity of the fovea.

However, when a tomographic image of a subject's eye is acquired using optical coherence tomography for the purpose of measuring the shape of the tissue in the fundus or the like, it is difficult to acquire the tomographic image with high reproducibility due to the amount of misalignment of alignment by the motion of the eye.

According to some embodiments of the present invention, a new technique for specifying shape of a tissue of a subject's eye with high reproducibility and high accuracy can be provided.

Referring now to the drawings, exemplary embodiments of an ophthalmologic information processing apparatus, an ophthalmologic apparatus, an ophthalmologic information processing method, and a program according to the present invention are described below. Any of the contents of the documents cited in the present specification and arbitrary known techniques may be applied to the embodiments below.

An ophthalmologic information processing apparatus according to embodiments acquires a plurality of tomographic images of a subject's eye. For example, the plurality of tomographic images is acquired by repeatedly performing optical coherence tomography on the subject's eye using an external ophthalmologic apparatus. The ophthalmologic information processing apparatus is capable of analyzing each of the acquired plurality of tomographic images to obtain a plurality of shape data (first shape data) of a predetermined tissue, and specifying (extrapolating, predicting) true shape data (second shape data) of the tissue from the obtained plurality of shape data. In some embodiments, the ophthalmologic information processing apparatus specifies the true shape data by performing statistical processing on the plurality of shape data. In some embodiments, the shape of a predetermined layer region is specified by one-dimensional, two-dimensional, or three-dimensional shape data of the predetermined layer region obtained by analyzing the tomographic image. The ophthalmologic apparatus according to some embodiments includes the above ophthalmologic information processing apparatus, and realizes the function of the ophthalmologic information processing apparatus.

By specifying the shape of the predetermined tissue of the subject's eye from the tomographic image or the shape data, the influence of an amount of misalignment of alignment (amount of alignment error) of the subject's eye with respect to the optical system for performing OCT can be reduced, and the shape of the tissue of the subject's eye can be specified with high reproducibility and high accuracy.

Examples of the shape of the tissue in the subject's eye include a shape of a tissue in the anterior segment, a shape of a tissue in the posterior segment, and the like. Examples of the shape of the tissue in the anterior segment include a shape of a cornea, a shape of an iris, a shape of a crystalline lens, a shape of a ciliary body, a shape of a ciliary zonule, a shape of an angle, and the like. Examples of the shape of the tissue in the posterior segment include a shape of the fundus (a predetermined layer region in the fundus), and the like. Hereinafter, shape of a predetermined layer region in a fundus will be described as an example of the shape of the tissue according to the embodiments. In some embodiments, the shape of the layer region in the fundus can be specified as the shape of the fundus. Examples of the layer region of the fundus include the inner limiting membrane, the nerve fiber layer, the ganglion cell layer, the inner plexiform layer, the inner nuclear layer, the outer plexiform layer, the outer nuclear layer, the external limiting membrane, the photoreceptor layer, the retinal pigment epithelium layer, the choroid, the sclera, the boundary surfaces of each layer region, and the like. However, the embodiments described after can be applied to the shape of any site of the eyeball other than the fundus. Further, in the following embodiments, shape data representing the shape of the fundus may be referred to as a shape profile. The shape profile is data representing a change in shape in a predetermined one-dimensional direction, a predetermined two-dimensional direction, or a predetermined three-dimensional direction.

The ophthalmologic information processing apparatus according to some embodiments calculates (extrapolates) a refractive power of a peripheral region outside a region including a fovea in the fundus using the shape of the fundus specified as described above. For example, the ophthalmologic information processing apparatus calculates the refractive power of the peripheral region outside the region including the fovea, based on a refractive power of the region including the fovea of the subject's eye and the specified shape of the fundus.

The ophthalmologic information processing apparatus according to the embodiments can calculate the refractive power of the above region using parameters of an eyeball model such as a known schematic eye (parameters representing optical characteristics of the eyeball). Examples of the parameter include axial length data, anterior chamber depth data, crystalline lens data (curvature of crystalline lens, thickness of crystalline lens, or the like) representing a shape of a crystalline lens, corneal shape data (corneal curvature radius, corneal thickness, or the like), and the like. The ophthalmologic information processing apparatus can build (form) a new eyeball model by replacing a part of the parameters of the eyeball model with the measured value of the subject's eye, and calculate the refractive power of the above region using the built new eyeball model. In some embodiments, the above parameter is obtained from an electronic health record system, a medical image archiving system, an external apparatus, or the like.

An ophthalmologic information processing method according to the embodiments includes one or more steps for realizing the processing executed by a processor (computer) in the ophthalmologic information processing apparatus according to the embodiments. A program according to the embodiments causes the processor to execute each step of the ophthalmologic information processing method according to the embodiments.

The term "processor" as used herein refers to a circuit such as, for example, a central processing unit (CPU), a graphics processing unit (GPU), an application specific integrated circuit (ASIC), and a programmable logic device (PLD). Examples of PLD include a simple programmable logic device (SPLD), a complex programmable logic device (CPLD), and a field programmable gate array (FPGA). The processor realizes the function according to the embodiments, for example, by reading out a computer program stored in a storage circuit or a storage device and executing the computer program.

In this specification, images acquired using OCT may be collectively referred to as "OCT images". Further, a measuring action for forming an OCT image is sometimes referred to as an OCT measurement. Data acquired by performing OCT scan is sometimes referred to as scan data.

Hereinafter, the case where the ophthalmologic apparatus according to the embodiments includes the ophthalmologic information processing apparatus will be described. The ophthalmologic apparatus is configured to acquire a tomographic image of the subject's eye by performing OCT on the subject's eye E. However, the ophthalmologic information processing apparatus according to the embodiments may be configured to acquire scan data (OCT data), the tomographic image, the shape profile described after, or the like from an external ophthalmologic apparatus.

The ophthalmologic apparatus according to some embodiments includes an OCT apparatus and is configured to perform position matching (alignment, tracking) between the subject's eye and an optical system for performing OCT. The ophthalmologic apparatus according to some embodiments further includes an objective refractometry apparatus. The ophthalmologic apparatus according to some embodiments includes a device (communication interface, input/output interface, etc.) that receives data from an external apparatus or a recording medium.

That is, the ophthalmologic apparatus according to the embodiments may be, for example, any one of the following: (A) an inspection apparatus that includes an objective refractometry apparatus (refractometry unit) and an OCT apparatus (OCT unit): (B) an inspection apparatus that does not include an objective refractometry apparatus (refractometry unit) but includes an OCT apparatus (OCT unit): (C) an information processing apparatus that includes neither an objective refractometry apparatus (refractometry unit) nor an OCT apparatus (OCT) unit.

Hereinafter, the left/right direction (i.e., horizontal direction) which is orthogonal to the optical axis of the optical system of the ophthalmologic apparatus is regarded as the x direction, the up/down direction (i.e., vertical direction) which is orthogonal to the axis is regarded as the y direction, and the optical axis direction (i.e., depth direction, front-back direction) is regarded as the z direction.

<Configuration>

Figure 2:
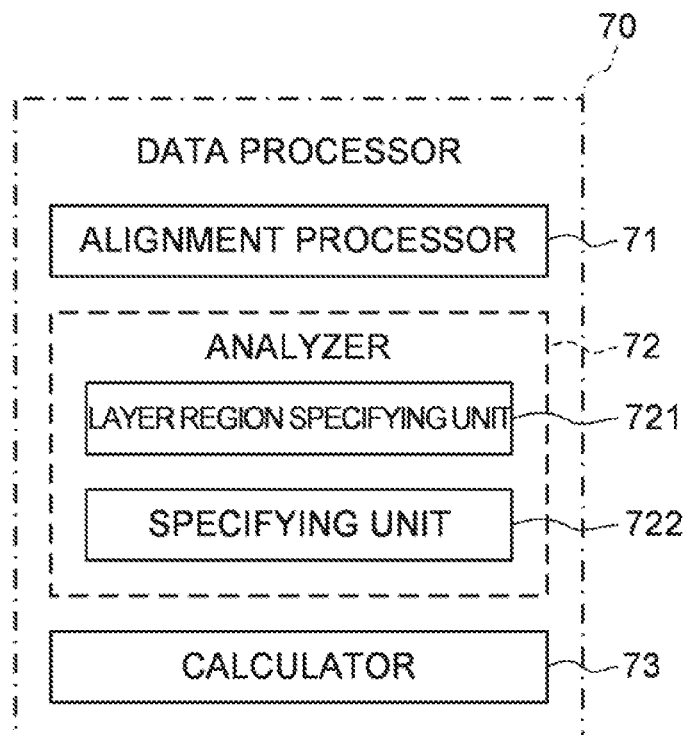
FIG. 2 is a schematic diagram illustrating an example of the configuration of the ophthalmologic apparatus according to the embodiments.
Figure 3:
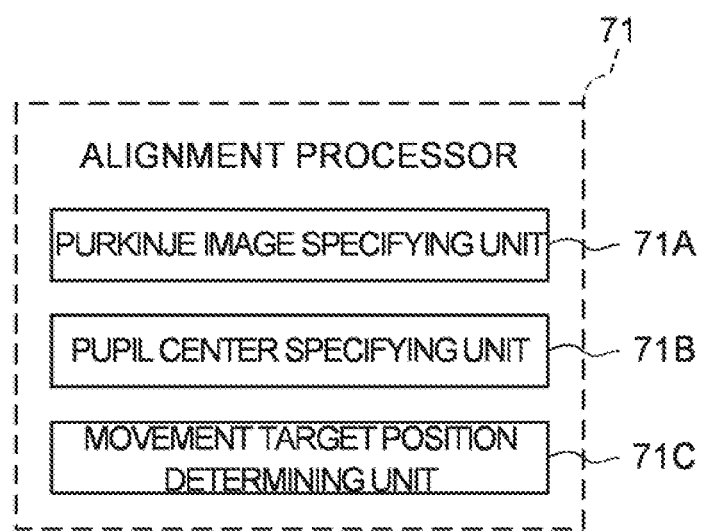
FIG. 3 is a schematic diagram illustrating an example of the configuration of the ophthalmologic apparatus according to the embodiments.
Figure 4:
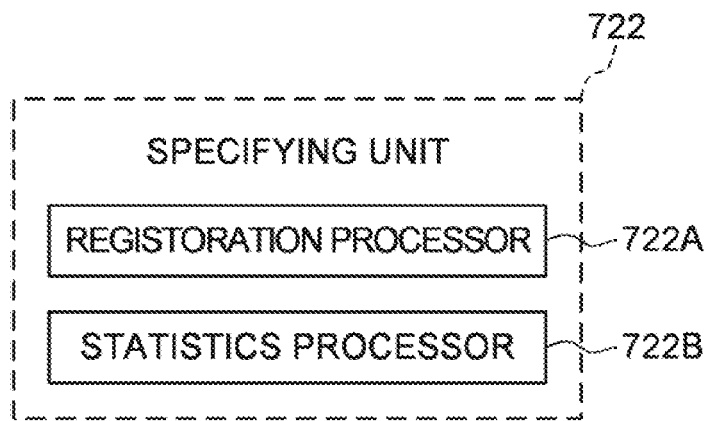
FIG. 4 is a schematic diagram illustrating an example of the configuration of the ophthalmologic apparatus according to the embodiments.
Figure 5:
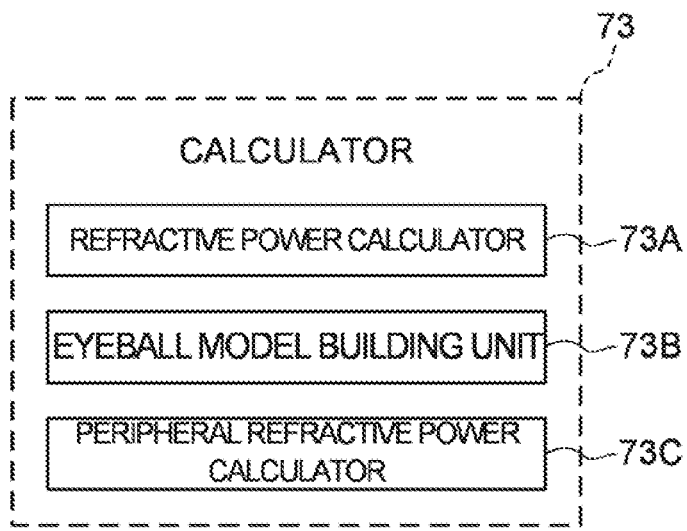
FIG. 5 is a schematic diagram illustrating an example of the configuration of the ophthalmologic apparatus according to the embodiments.

FIGS. 1 to 5 illustrate examples of the configuration of the ophthalmologic apparatus according to the embodiments. FIG. 1 is a schematic block diagram illustrating an example of the configuration of the ophthalmologic apparatus according to the embodiments. FIG. 2 shows a functional block diagram representing a configuration example of a data processor 70 in FIG. 1. FIG. 3 shows a functional block diagram representing a configuration example of an alignment processor 71 in FIG. 2. FIG. 4 shows a functional block diagram representing a configuration example of a specifying unit 722 in FIG. 2. FIG. 5 shows a functional block diagram representing a configuration example of a calculator 73 in FIG. 2.

The ophthalmologic apparatus 1 is an inspection apparatus that includes an objective refractometry apparatus (refractometry unit) and an OCT apparatus (OCT unit). The ophthalmologic apparatus 1 includes a measurement unit 10, a control processor 50, a movement mechanism 90, and an imaging unit 100. The measurement unit 10 includes a refractometry unit 20, an OCT unit 30, an alignment light projection unit 40, and beam splitters BS1 and B2. The control processor 50 includes an image forming unit 60, a data processor 70, and a controller 80.

(Refractometry Unit 20)

The refractometry unit 20 objectively measures a refractive power of a subject's eye E under the control of the controller 80. The refractometry unit 20 includes an optical system provided with one or more optical members for performing objective refractometry. The refractometry unit 20 has the same configuration as a known refractometer, for example. An exemplary refractometer (not shown in the figure) includes a projection system and a light reception system as disclosed in Japanese Unexamined Patent Application Publication No. 2016-077774.

A projection system of the refractometry unit 20 is configured to project light emitted from a light source onto a fundus Ef of the subject's eye E. The projection system projects the light from the light source onto the fundus Ef through a collimate lens, a focusing lens, a relay lens, a pupil lens, a perforated prism, a decentered prism (eccentric prism), an objective lens, and the like, for example.

A light reception system of the refractometry unit 20 projects reflected light from the fundus Ef onto an imaging element through the objective lens, the decentered prism, the perforated prism, other pupil lenses, other relay lenses, another focusing lens, a conical prism, an imaging lens, and the like. Thereby, a ring pattern image formed on an imaging surface of the imaging element is detected.

In some embodiments, the refractometry unit 20 is configured to project ring-shaped light onto the fundus Ef and to detect the ring pattern image formed by the reflected light from the fundus Ef. In some embodiments, the refractometry unit 20 is configured to project bright spot onto the fundus Ef, to convert the reflected light from the fundus Ef into ring-shaped light, and to detect the ring pattern image formed by the converted ring-shaped light.

(OCT Unit 30)

The OCT unit 30 acquires OCT data (scan data) by applying OCT scan to the subject's eye E under the control of the controller 80. The OCT data may be interference signal data, reflection intensity profile data obtained by applying Fourier transformation to the interference signal data, image data obtained by imaging the reflection intensity profile data.

The OCT method that can be performed by the OCT unit 30 is typically Fourier domain OCT. Fourier domain OCT may be either spectral domain OCT or swept source OCT. The swept source OCT is a method that splits light from a wavelength tunable light source into measurement light and reference light; superposes returning light of the measurement light projected onto the subject's eye from the subject's eye with the reference light to generate interference light; detects the interference light with an optical detector; and applies the Fourier transformation etc. to detection data (interference signal data) acquired in accordance with the sweeping of wavelengths and the scanning of the measurement light to form reflection intensity profile data. On the other hand, the spectral domain OCT is a method that splits light from a low coherence light source (broadband light source) into measurement light and reference light; superposes returning light of the measurement light projected onto the subject's eye from the subject's eye with the reference light to generate interference light; detects the spectral distribution of the interference light with a spectrometer; and applies the Fourier transformation etc. to detection data (interference signal data) detected by the spectrometer to form reflection intensity profile data. That is, the swept source OCT is an OCT method for acquiring the spectral distribution by time division, and the spectral domain OCT is an OCT method for acquiring the spectral distribution by space division.

The OCT unit 30 includes an optical system provided with one or more optical members for performing OCT measurement. The OCT unit 30 has the same configuration as a known OCT apparatus, for example. An exemplary OCT apparatus (not shown in the figure) includes a light source, an interference optical system, a scan system, and a detection system as disclosed in Japanese Unexamined Patent Application Publication No. 2016-077774.

Light output from the light source is split into the measurement light and the reference light by the interference optical system. The reference light is guided by a reference arm. The measurement light is projected onto the subject's eye E (for example, the fundus Ef) through a measurement arm. The measurement arm is provided with the scan system. The scan system includes, for example, an optical scanner and is capable of deflecting the measurement light one-dimensionally or two-dimensionally. The optical scanner includes one or more galvano scanners. The scan system deflects the measurement light according to a predetermined scan mode.

The controller 80 described after can control the scan system according to the scan mode. Examples of the scan mode include line scan, raster scan (three-dimensional scan), circle scan, concentric scan, radial scan, cross scan, multi cross scan, spiral scan, and the like. The line scan is a scan pattern along a linear trajectory. The raster scan is a scan pattern consisting of a plurality of line scans arranged parallel to one another. The circle scan is a scan pattern along a circular trajectory. The concentric scan is a scan pattern consisting of a plurality of circle scans arranged concentrically. The radial scan is a scan pattern consisting of a plurality of line scans arranged radially. The cross scan is a scan pattern consisting of two line scans arranged orthogonal to one another. The multi cross scan is a scan pattern consisting of two line scan groups (for example, each groups includes five lines parallel to one another) orthogonal to one another. The spiral scan is a scan pattern extending in a spiral manner from the center.

The measurement light projected onto the fundus Ef is scattered and reflected at various depth positions (layer boundaries, etc.) of the fundus Ef. The returning light of the measurement light from the subject's eye E is combined with the reference light by the interference optical system. The returning light of the measurement light and the reference light generates the interference light according to the principle of superposition. This interference light is detected by the detection system. The detection system typically includes the spectrometer in case of spectral domain OCT. The detection system typically includes a balanced photodiode and a data acquisition system (DAQ) in case of swept source OCT.

(Alignment Light Projection Unit 40)

The alignment light projection unit 40 projects alignment light for performing position matching between the subject's eye E and the measurement unit 10 (OCT unit, the optical system of the apparatus). The alignment light projection unit 40 includes an alignment light source and a collimator lens. An optical path of the alignment light projection unit 40 is coupled with an optical path of the refractometry unit 20 by the beam splitter BS2. Light emitted from the alignment light source passes through the collimator lens, is reflected by the beam splitter BS2, and is projected onto the subject's eye E through the optical path of the refractometry unit 20.

In some embodiments, as disclosed in Japanese Unexamined Patent Application Publication No. 2016-077774, the reflected light from the cornea Ec (anterior segment) of the subject's eye E is guided to the light reception system of the refractometry unit 20 through the optical path of the refractometry unit 20.

An image (bright spot image) based on the reflected light by the cornea Ec of the subject's eye E is included in the anterior segment image acquired by the imaging unit 100. For example, the control processor 50 controls the display unit (not shown in Figure) to display an alignment mark and the anterior segment image including the bright spot image on the display screen of the display unit. In the case of performing XY alignment (alignment in vertical and horizontal directions) manually, a user can perform an operation for moving the optical system so as to guide the bright spot image in the alignment mark. In the case of performing Z alignment (alignment in front-back direction) manually, a user can perform the operation for movement of the optical system while referring to the anterior segment image displayed on the display screen of the display unit. In the case of performing alignment automatically, the controller 80 controls the movement mechanism 90 to relatively move the measurement unit 10 (optical system) with respect to the subject's eye E so as to cancel the displacement between the alignment mark and the position of the bright spot image. Further, the controller 80 can control the movement mechanism 90 to move the measurement unit 10 (optical system) with respect to the subject's eye E so as to satisfy a predetermined alignment completion condition based on a position of a predetermined site (for example, pupil center position) of the subject's eye E and the position of the bright spot image.

(Beam Splitter BS1)

The beam splitter BS1 coaxially couples the optical path of the optical system (interference optical system, etc.) of the OCT unit 30 with the optical path of the optical system (projection system and light reception system) of the refractometry unit 20. For example, a dichroic mirror is used as the beam splitter BS1.

(Beam Splitter BS2)

The beam splitter BS2 coaxially couples the optical path of the optical system of the alignment light projection unit 40 with the optical path of the optical system (projection system and light reception system) of the refractometry unit 20. For example, a half mirror is used as the beam splitter BS2.

In some embodiments, the ophthalmologic apparatus 1 has a function (fixation projection system) that presents a fixation target, which is used for guiding a visual line of the subject's eye, to the subject's eye E under the control of the controller 80. The fixation target may be an internal fixation target presented to the subject's eye E or an external fixation target presented to the fellow eye. In some embodiments, an optical path of the fixation projection system and the optical path of the interference optical system of the OCT unit 30 are configured to coaxially coupled by an optical path coupling member (for example, beam splitter) arranged between the OCT unit 30 and the beam splitter BS1.

A projection position of the fixation target in the fundus Ef projected by the fixation target projection system can be changed under the control of the controller 80. In some embodiments, the fixation target is projected onto the measurement optical axes of coaxially coupled the optical system of the refractometry unit 20 and the optical system of the OCT unit 30. In some embodiments, the fixation target is projected at a position deviated from the measurement optical axis on the fundus Ef.

(Imaging Unit 100)

The imaging unit 100 includes one or more anterior segment cameras for imaging the anterior segment of the subject's eye E. The imaging unit 100 acquires the anterior segment image which is the front image of the subject's eye E. In some embodiments, at least one anterior segment illumination light source (infrared light source or the like) is provided in the vicinity of the one or more anterior segment cameras. For example, for each anterior segment cameras, the anterior segment illumination light source is provided in the upper vicinity and the lower vicinity of the anterior segment camera, respectively.

The ophthalmologic apparatus 1 can perform position matching (alignment) of the measurement unit 10 (optical system) with respect to the subject's eye E using the front image acquired by the imaging unit 100. In some embodiments, the ophthalmologic apparatus 1 specifies a three-dimensional position of the subject's eye E by analyzing the front image acquired by imaging the anterior segment of the subject's eye E, and performs position matching by relatively moving the measurement unit 10 based on the specified three-dimensional position. In some embodiments, the ophthalmologic apparatus 1 performs position matching so as to cancel the displacement between a characteristic position of the subject's eye E and a position of the image formed by the alignment light projected by the alignment light projection unit 40.

As described above, the imaging unit 100 includes one or more anterior segment cameras. In case that the imaging unit 100 includes a single anterior segment camera, the ophthalmologic apparatus 1 analyzes the acquired front image, and specifies a two-dimensional position of the subject's eye E in a plane orthogonal to the optical axis of the measurement unit 10 (plane defined by the horizontal direction (X direction) and the vertical direction (Y direction)). In this case, the alignment optical system for specifying a position of the subject's eye E in the optical axis direction of the measurement unit 10 is provided in the ophthalmologic apparatus 1. Examples of such an alignment optical system includes an optical system of an optical lever system as disclosed in Japanese Unexamined Patent Application Publication No. 2016-077774. The ophthalmologic apparatus 1 can specify the three-dimensional position of the subject's eye E from the position of the subject's eye in the (measurement) optical axis of the measurement unit 10 and the above two-dimensional position, using alignment optical system like this.

In case that the imaging unit 100 includes two or more anterior segment cameras, two or more anterior segment cameras photograph the anterior segment of the subject's eye E from different directions. The two or more anterior segment cameras can substantially simultaneously photograph the anterior segment from two or more different directions. The phrase "substantially simultaneously" indicates that the deviation in photography timings at a level where the eye movement is negligible is allowed in the photography with two or more anterior segment cameras. Thereby, images of the subject's eye E located in substantially the same position (orientation) can be acquired by the two or more anterior segment cameras. The ophthalmologic apparatus 1 analyzes the front images of the subject's eye E, specifies the characteristic position of the subject's eye E, and specifies the three-dimensional position of the subject's eye E from the positions of the two or more anterior segment cameras and the characteristic position.

Photography using the two or more anterior segment cameras may be moving image photography or still image photography. In the case of moving image photography, substantially simultaneous photography of the anterior segment as described above can be realized by performing control for synchronizing photography start timings, controlling the frame rates or the capture timings of respective frames, or the like. On the other hand, in the case of still image photography, this can be realized by performing control for synchronizing photography timings.

In the following, it is assumed that the imaging unit 100 includes two anterior segment cameras. Each of the two anterior segment cameras is located at a position off the measurement optical axis (optical axis of the OCT unit 30) as disclosed in Japanese Unexamined Patent Application Publication No. 2013-248376. In some embodiments, one of the two anterior segment cameras is an imaging element in the light reception system of the refractometry unit 20.

(Control Processor 50)

The control processor 50 performs various calculations and various controls for operating the ophthalmologic apparatus 1. The control processor 50 includes one or more processors and one or more storage devices. Examples of the storage device include random access memory (RAM), read only memory (ROM), hard disk drive (HDD), solid state drive (SSD), and the like. The storage device stores various computer programs. The calculation and control according to the present examples are realized by operating the processor based on it.

(Image Forming Unit 60)

The image forming unit 60 forms an image (tomographic image, etc.) of the subject's eye E based on the scan data acquired by performing OCT on the subject's eye E. The image forming unit 60 builds OCT data (typically, image data) based on detection data detected by the detection system of the OCT unit 30. The image forming unit 60, similar to conventional OCT data processing, builds the reflection intensity profile data in A line (path of the measurement light in the subject's eye E), by applying filter processing, fast Fourier transformation (FFT), and the like to the detection data. In addition, the image forming unit 60 builds the image data of each A line (A scan data) by applying image processing (image expression) to this reflection intensity profile data. In some embodiments, the function of the image forming unit 60 is realized by a processor.

In some embodiments, at least part of the function of the image forming unit 60 is provided in the OCT unit 30.

(Data Processor 70)

The data processor 70 executes various data processing. The data processor 70 can build (form) B scan data by arranging a plurality of A scan data according to the scan mode performed by the scan system. In some embodiments, the data processor 70 performs superposition processing of the two or more B scan data. The data processor 70 can build stack data by arranging a plurality of B scan data according to the scan mode performed by the scan system. The data processor 70 build volume data (voxel data) from the stack data. The data processor 70 can render the stack data or the volume data. Examples of rendering method include volume rendering, multi-planar reconstruction (MPR), surface rendering, projection, and the like.

The data processor 70 can execute processing for performing position matching of the measurement unit 10 with respect to the subject's eye E. Examples of the processing for performing position matching include analysis processing of the front image of the subject's eye E acquired using the imaging unit 100, calculation processing of the position of the subject's eye E, calculation processing of the displacement of the measurement unit 10 with respect to the subject's eye E, and the like.

In addition, the data processor 70 can acquire shape data (shape profile) representing the shape of the fundus Ef of the subject's eye E from each of the plurality of tomographic images of the subject's eye E obtained by repeatedly performing OCT measurement after position matching (alignment) of the measurement unit 10 with respect to the subject's eye E, and generate shape data representing the true shape of the fundus Ef from the acquired plurality of shape data. For example, the shape data representing the true shape of the fundus Ef is obtained by performing statistical processing on the acquired plurality of shape data. Further, the data processor 70 can calculate refractive power of a peripheral region of a region including a fovea of the subject's eye E using the specified shape of the fundus Ef (shape data representing the true shape of the fundus Ef).

As shown in FIG. 2, such as the data processor 70 includes an alignment processor 71, an analyzer 72, and a calculator 73.

(Alignment Processor 71)

The alignment processor 71 executes processing for performing position matching (alignment) of the measurement unit 10 with respect to the subject's eye E. In some embodiments, the alignment processor 71 corrects distortion of the photographic images captured by the anterior segment cameras, and executes processing for performing above position matching using the captured photographic image(s) whose distortion has (have) been corrected. In this case, the alignment processor 71 corrects the distortion of the photographic image(s) based on the aberration information stored in a storage unit provided in the control processor 50 or the data processor 70. This processing is performed by, for example, known image processing technology based on a correction factor for correcting distortion aberration.

As shown in FIG. 3, the alignment processor 71 includes a Purkinje image specifying unit 71A, a pupil center specifying unit 71B, and a movement target position determining unit 71C.

(Purkinje Image Specifying Unit 71A)

By projecting the alignment light onto the anterior segment of the subject's eye E using the alignment light projection unit 40, a Purkinje image is formed. The Purkinje image is formed in a position displaced from the corneal apex in the optical axis direction (z direction) by half of the radius of the corneal curvature.

The anterior segment onto which the alignment light is projected is substantially simultaneously photographed by the two anterior segment cameras. The Purkinje image specifying unit 71A specifies the Purkinje image (image region corresponding to the Purkinje image) by analyzing each of the two photographic images substantially simultaneously acquired using the two anterior segment cameras. This specifying processing includes, for example as in the conventional case, a threshold processing related to a pixel value for searching for a bright spot (pixel having high brightness) corresponding to the Purkinje image. Thereby, the image regions in the photographic images corresponding to the Purkinje image are specified.

The Purkinje image specifying unit 71A can obtain a position of a representative point in the image region corresponding to the Purkinje image. The representative point may be a center point or a center of gravity point of the image region, for example. In this case, the Purkinje image specifying unit 71A can obtain an approximate circle or an approximate ellipse of the periphery of the image region, and can obtain the center point or the center of gravity point of the approximate circle or the approximate ellipse.

Each of the two photographic images is an image obtained by photographing the anterior segment from a diagonal direction. In each of the photographic images, a pupil region and a Purkinje image are depicted. The Purkinje image specifying Unit 71A specifies the Purkinje images in the two photographic images.

Here, the two photographic images are images obtained by photographing from directions different from the optical axis of the measurement unit 10 (objective lens). When XY alignment is substantially matched, the Purkinje images in the two photographic images are formed on the optical axis of the measurement unit 10.

Visual angles (angles with respect to the optical axis of the measurement unit 10) of the two anterior segment cameras are known and the photographing magnification is also known. Thereby, the relative position (three-dimensional position in actual space) of the Purkinje image formed in the anterior segment with respect to the ophthalmologic apparatus 1 (imaging unit 100) can be obtained based on the positions of the Purkinje images in the two photographic images.

Further, the relative position between the characteristic position of the subject's eye E and the Purkinje image formed in the anterior segment can be obtained based on the relative position (misalignment amount) between the characteristic position of the subject's eye E and the position of the Purkinje image in each of the two photographic images.

The Purkinje image specifying unit 71A specifies the position of the Purkinje image specified as above. The position of the Purkinje image may include at least a position in the x direction (x coordinate value) and a position in the y direction (y coordinate value), or may further include a position in the z direction (z coordinate value).

(Pupil Center Specifying Unit 71B)

The pupil center specifying unit 71B specifies a position in the photographic image corresponding to a predetermined characteristic position of the anterior segment by analyzing each of photographic images (or the images corrected for distortion aberration) obtained by the anterior segment cameras. In the present embodiment, the pupil center of the subject's eye E is specified. It should be noted that the center of gravity of the pupil may be obtained as the pupil center. It is also possible to configure such that the characteristic position other than the pupil center (the center of gravity of the pupil) is specified.

The pupil center specifying unit 71B specifies the image region (pupil region) corresponding to the pupil of the subject's eye E based on the distribution of pixel values (luminance values etc.) in the photographic image. Generally, the pupil is represented with lower luminance compared to other sites, and therefore, the pupil region may be specified by searching an image region with low luminance. At this time, the pupil region may be specified by taking the shape of the pupil into consideration. That is, it is possible to configure such that the pupil region is specified by searching for a substantially circular image region with low luminance.

Next, the pupil center specifying unit 71B specifies the center position of the specified pupil region. As mentioned above, the pupil is substantially circular. Accordingly, by specifying the contour of the pupil region and then specifying the center position of an approximate ellipse of this contour, this may be used as the pupil center. Instead, by obtaining the center of gravity of the pupil region, this center of gravity may be used as the pupil center.

Note that, even when other characteristic positions are employed, the position of the characteristic position can be specified based on the distribution of pixel values in the photographic image in the same manner as mentioned above.

The pupil center specifying unit 71B specifies the three-dimensional position of the pupil center of the subject's E, based on the positions of the two anterior segment cameras (and the photographing magnification) and the positions of the specified pupil center in the two photographic images.

For example, the resolution of photographic images obtained by the two anterior segment cameras is expressed by the following expressions.

$xy$ resolution (planar resolution): $\Delta xy = H \times \Delta p / f$ $z$ resolution (depth resolution): $\Delta z = H \times H \times \Delta p / (B \times f)$ Here, the distance (base line length) between the two anterior segment cameras is represented as "B", the distance (photographing distance) between the base line of the two anterior eye cameras and the pupil center of the subject's eye E is represented as "H", the distance (screen distance) between each anterior segment camera and its screen plane is represented as "f", and the pixel resolution is represented as "Δp".

The pupil center specifying unit 71B applies known trigonometry to the positions of the two anterior segment cameras (these are known) and positions corresponding to the pupil center in the two photographic images, thereby calculating the three-dimensional position of the pupil center.

(Movement Target Position Determining Unit 71C)

The movement target position determining unit 71C determines the movement target position of the measurement unit 10 (optical system of the apparatus) based on the position of the Purkinje image specified by the Purkinje image specifying unit 71A and the position of the pupil center specified by the pupil center specifying unit 71B. For example, the movement target position determining unit 71C obtains the difference between the position of the specified Purkinje image and the position of the specified pupil center, and determines the movement target position so that the obtained difference satisfies a predetermined alignment completion condition.

The controller 80 described after controls the movement mechanism 90 based on the movement target position determined by the movement target position determining unit 71C.

(Analyzer 72)

As shown in FIG. 2, the analyzer 72 includes a layer region specifying unit 721, and a specifying unit 722. The layer region specifying unit 721 specifies a predetermined layer region (a predetermined tissue) in the acquired tomographic image of subject's eye E. The specifying unit 722 specifies the shape of the fundus Ef based on the predetermined layer region specified by the layer region specifying unit 721.

(Layer Region Specifying Unit 721)

The layer region specifying unit 721 specifies the predetermined layer region of the fundus Ef by analyzing the tomographic image of the subject's eye E. Examples of the layer region of the fundus Ef include the inner limiting membrane, the nerve fiber layer, the ganglion cell layer, the inner plexiform layer, the inner nuclear layer, the outer plexiform layer, the outer nuclear layer, the external limiting membrane, the photoreceptor layer, the retinal pigment epithelium layer, the choroid, the sclera, the boundary surfaces of each layer region, and the like.

Processing of specifying the predetermined layer region from the tomographic image typically includes segmentation processing. The segmentation processing is known processing for specifying a partial region in a tomographic image. The layer region specifying unit 721 performs, for example, segmentation processing based on a brightness value of each pixel in the tomographic image. That is, each of the layer regions of the fundus Ef has a characteristic reflectance, and image regions corresponding to these layer regions also have characteristic brightness values. The layer region specifying unit 721 can specify a target image region (layer region) by performing segmentation processing based on these characteristic brightness values.

The layer region specifying unit 721 outputs data representing the shape of the specified predetermined layer region as the shape profile of the layer region. In some embodiments, the shape profile is one-dimensional, two-dimensional, or three-dimensional shape data representing a change in the shape of the fundus Ef in at least one direction of the x direction, the y direction, and the z direction.

For example, the layer region specifying unit 721 can specify the retinal pigment epithelium layer (or OS-RPE boundary surface).

(Specifying Unit 722)

The specifying unit 722 specifies the shape of the fundus Ef from the shape data (shape profile) obtained by the layer region specifying unit 721. The specifying unit 722 specifies the shape data representing the true shape from the plurality of shape data of the predetermined layer region obtained from each of the plurality of tomographic images acquired by repeatedly performing OCT measurement. The specifying unit 722 obtains, for example, the shape data representing the true shape by performing statistical processing on the plurality of shape data. In some embodiments, the specifying unit 722 generates a new shape profile one-dimensionally (two-dimensionally or three-dimensionally) representing the true shape of the layer region from the plurality of shape profiles one-dimensionally (two-dimensionally or three-dimensionally) representing the shape of the layer region. The new shape profile is, for example, shape data which is capable of specifying the shape of the layer region using new parameters such as curvature of the fundus, tilt of the fundus, and the like.

As shown in FIG. 4, such the specifying unit 722 includes a registration processor 722A and a statistics processor 722B.

(Registration Processor 722A)

The registration processor 722A performs registration (position matching) of the plurality of shape profiles obtained from each of the plurality of tomographic images acquired by repeatedly performing OCT measurement. The registration processor 722A performs registration on the plurality of shape profiles in the xy directions and the z direction. The xy directions are directions orthogonal to (intersecting) the measurement optical axis of the OCT unit 30. The z direction is a direction of the measurement optical axis of the OCT unit 30.

In some embodiments, the registration processor 722A obtains a shift amount based on a correlation value of the plurality of tomographic images, and performs registration of the plurality of shape profiles based on the obtained shift amount.

For example, the registration processor 722A calculates the correlation value of the obtained plurality of tomographic images using a known correlation function. The registration processor 722A changes the shift amount of at least one of the plurality of tomographic images (in the depth direction, or the direction orthogonal to the depth direction) to calculate the correlation value again. The registration processor 722A determines whether to update the shift amount to calculate a new correlation value based on the comparison result of an original correlation value and the correlation value newly calculated. The registration processor 722A repeats the calculation of the correlation value and the comparison to obtain the shift amount (including shift direction) at which the correlation value becomes maximum, and performs registration of at least one of the plurality of shape profiles based on the obtained shift amount.

In some embodiments, the registration processor 722A performs registration of the plurality of shape profiles based on constant terms of polynomials obtained by performing polynomial approximation on each of the plurality of shape profiles.

For example, the registration processor 722A performs polynomial approximation on each of the acquired plurality of shape profiles. For each of the shape profiles, the registration processor 722A obtains an approximate polynomial by obtaining a coefficient of each order so that the difference between the shape profile and a polynomial of the first order or the high order having the scan position as a variable becomes minimum. The registration processor 722A obtains the constant term from the obtained approximate polynomial, and shifts the shape profile by the shift amount corresponding to the obtained constant term in at least one of the xy directions and the z direction. Each of the plurality of shape profile is shifted in the same manner. Thereby, registration of the plurality of shape profiles is performed.

In some embodiments, the registration processor 722A extracts characteristic parts from the acquired plurality of shape profiles, and performs registration of the plurality of shape profiles with reference to the extracted characteristic parts.

For example, the registration processor 722A extracts a characteristic part from each of the acquired plurality of shape profiles. In some embodiments, a characteristic shaped part of the shape profile is specified as the characteristic part. In some embodiments, the characteristic part of the shape profile, the characteristic part corresponding to the characteristic region of the subject's eye E specified by analyzing the tomographic image or the front image (fundus image) of the subject's eye E, is specified. Examples of the characteristic shaped parts include a characteristic site (fovea, macular region, optic disc) of the subject's eye, a lesion of the subject's eye, and the like. In some embodiments, a change point of the shape of the shape profile is specified as the characteristic part. In some embodiments, a calculated value obtained from the shape profile is extracted as the characteristic part. Examples of the calculated value include a center of curvature, position of the center of gravity, a center position, and the like. The registration processor 722A performs registration on at least one of the plurality of shape profiles so that both of the positions of the extracted characteristic part and the orientations of the extracted characteristic part coincide each other.

(Statistics Processor 722B)

The statistics processor 722B performs statistical processing on the plurality of shape profiles on which registration has been performed by the registration processor 722A, and outputs the shape profile after statistical processing as a shape profile representing true shape of the predetermined layer region. Examples of the statistical processing include averaging processing, median calculation processing, mode calculation processing, maximum likelihood value calculation processing, maximum calculation processing, minimum calculation processing, and the like. The statistical processing may include representative value selection processing.

Figure 6:
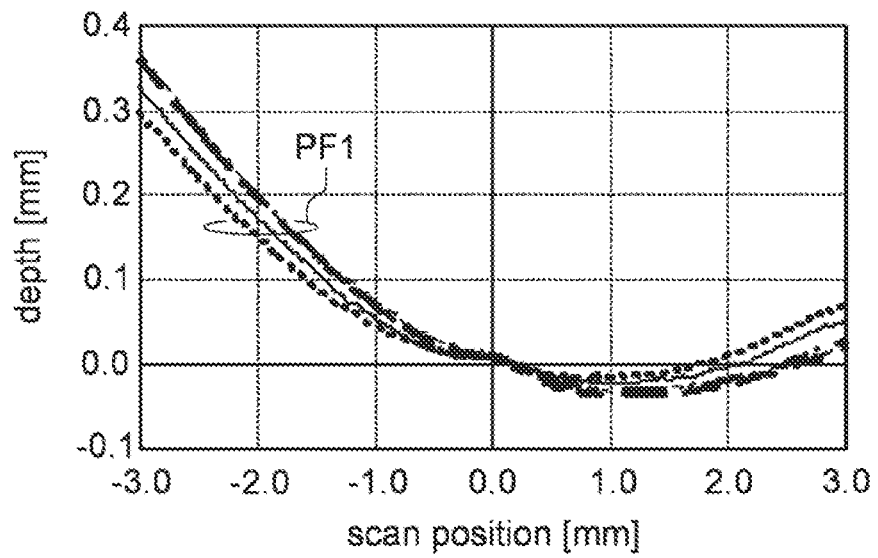
FIG. 6 is a schematic diagram for explaining an operation of the ophthalmologic apparatus according to the embodiments.
Figure 7:
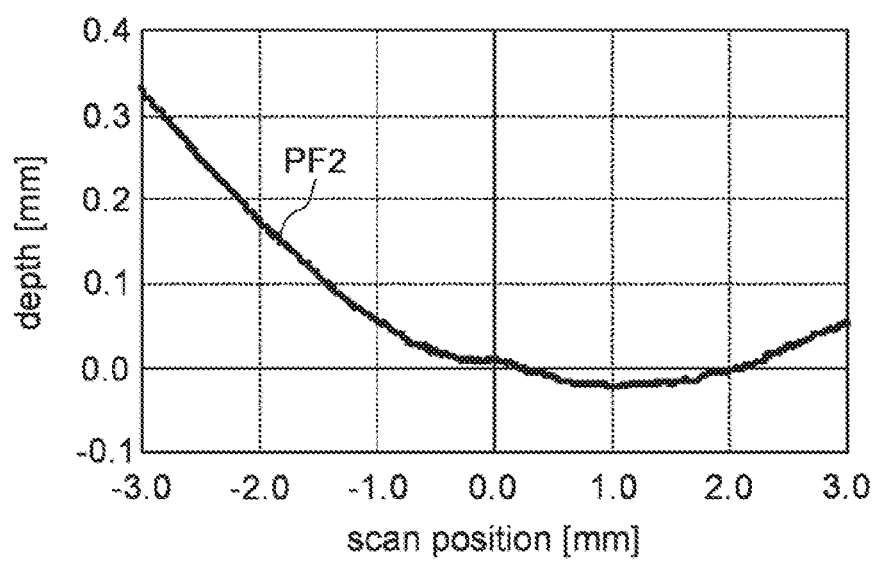
FIG. 7 is a schematic diagram for explaining an operation of the ophthalmologic apparatus according to the embodiments.

FIGS. 6 and 7 show diagrams describing the operation of the statistics processor 722B according to the embodiments. FIG. 6 shows an example of the shape profile on which registration has been performed by the registration processor 722A. In FIGS. 6 and 7, the horizontal axis represents the scan position (for example, the position in the x direction), and the vertical axis represents the depth position (for example, the position in the z direction). FIG. 7 shows an example of the shape profile obtained by performing average processing by the statistics processor 722B.

The statistics processor 722B obtains a statistical value for each scan position for the plurality shape profiles (shape profiles PF1 shown in FIG. 6) on which registration has been performed by the registration processor 722A. The statistics processor 722B outputs a shape profile (shape profile PF2 shown in FIG. 7) representing a change in the obtained statistical values as the profile obtained by performing statistical processing on the above plurality of shape profiles.

In case of assuming that the variations of the plurality of shape profiles obtained by repeatedly performing OCT measurement follow the Gaussian distribution model with reference to the position where the scan position is zero, averaging processing can be used as the statistical processing. In this case, the statistics processor 722B obtains an average value for each scan position for the plurality shape profiles on which registration has been performed by the registration processor 722A. The statistics processor 722B outputs a profile representing a change in the obtained average values as the profile obtained by averaging the above plurality of shape profiles.

In some embodiments, the median calculation processing can be used as the statistical processing. In this case, the statistics processor 722B obtains a median for each scan position for the plurality shape profiles on which registration has been performed by the registration processor 722A. The statistics processor 722B outputs a profile representing a change in the obtained median as the profile obtained by performing median calculation processing on the above plurality of shape profiles.

In some embodiments, the mode calculation processing can be used as the statistical processing. In this case, the statistics processor 722B obtains a mode for each scan position for the plurality shape profiles on which registration has been performed by the registration processor 722A. The statistics processor 722B outputs a profile representing a change in the obtained mode as the profile obtained by performing mode calculation processing on the above plurality of shape profiles.

In case of assuming that the variations of the plurality of shape profiles follow an arbitrary probability distribution model (including an asymmetric probability distribution model with reference to the position where the scan position is zero), maximum likelihood value calculation processing can be used as the statistical processing. In this case, the statistics processor 722B obtains a maximum likelihood value for each scan position for the plurality shape profiles on which registration has been performed by the registration processor 722A. The statistics processor 722B outputs a profile representing a change in the obtained maximum likelihood values as the profile obtained by performing maximum likelihood value calculation processing on the above plurality of shape profiles. It should be noted that the above average value is one of the maximum likelihood values.

In some embodiments, the representative value selection processing can be used as the statistical processing. In this case, the statistics processor 722B obtains a representative value for each scan position for the plurality shape profiles on which registration has been performed by the registration processor 722A. The representative value is data representing the depth position of any one of the plurality of shape profiles. The representative value is obtained by selecting from the data representing the depth positions of the plurality of shape profiles, based on a predetermined reference value such as at least one shape of the plurality of shape profiles, statistics (variance, standard deviation, etc.) of the plurality of shape profiles, or the like. The statistics processor 722B outputs a profile representing a change in the obtained representative values as the profile obtained by performing representative value selection processing on the above plurality of shape profiles.

In some embodiments, the statistics processor 722B specifies the shape profile representing the true shape from the plurality of shape profiles acquired from each of the plurality of tomographic images without registration performed by the registration processor 722A.

(Calculator 73)

The calculator 73 calculates a refractive power obtained by objectively measuring the subject's eye E, and calculates a refractive power of the peripheral region of the region including a fovea of the subject's eye E based on the calculated refractive power and the shape (shape profile) of the fundus Ef specified by the specifying unit 722. In some embodiments, the calculator 73 calculates the refractive power of the peripheral region of a region including the fovea of the subject's eye based on the calculated refractive power and a parameter representing optical characteristics of the subject's eye corresponding to the shape of the fundus specified by the specifying unit 722. The calculator 73 can build an eyeball model based on the parameter representing optical characteristics of the subject's eye corresponding to the shape of the fundus Ef specified by the specifying unit 722, and can calculate the refractive power of the above peripheral region from the built eyeball model and the calculated refractive power.

As shown in FIG. 5, the calculator 73 includes a refractive power calculator 73A, an eyeball model building unit 73B, and a peripheral refractive power calculator 73C.

(Refractive Power Calculator 73A)

The refractive power calculator 73A calculates the refractive power by processing the output from the imaging element of the light reception system of the refractometry unit 20.

In some embodiments, the refractive power calculator 73A executes a process of specifying an elliptical shape by elliptically approximating the ring pattern image acquired by the imaging element and a process of obtaining the refractive power (measurement data) based on the specified elliptical shape and a diopter for focus adjustment for the focusing lens and the like.

In some embodiments, the refractive power calculator 73A executes a process of obtaining brightness distribution in the image in which the ring pattern image acquired by the imaging element is depicted, a process of obtaining a position of the center of gravity of the ring pattern image from the obtained brightness distribution, a process of obtaining brightness distribution along a plurality of scanning directions extending radially from the obtained position of the center of gravity, a process of specifying a ring pattern image from the obtained brightness distribution along the plurality of scanning directions, a process of obtaining an approximate ellipse from the specified ring pattern image, and a process of calculating the refractive power by substituting the major axis and the minor axis of the obtained approximate ellipse into a known expression.

In some embodiments, the refractive power calculator 73A executes a process of obtaining a deflection (position shift, deformation, etc.) from the reference pattern of the ring pattern image acquired by the imaging element, and a process of obtaining the refractive power from this deflection.

In some embodiments, a spherical power S, an astigmatic power C, and an astigmatic axis angle C is calculated as the refractive power. In some embodiments, an equivalent spherical power SE (=S+C/2) is calculated as the refractive power.

(Eyeball Model Building Unit 73B)

The eyeball model building unit 73B builds an eyeball model. The eyeball model building unit 73B can build (form) a new eyeball model by applying separately acquired parameters to an eyeball model such as a known schematic eye.

The eyeball model building unit 73B can build a new eyeball model by applying an intraocular distance of the subject's eye E acquired by OCT measurement or the like as the measured parameter to an eyeball model such as a known schematic eye. In this case, the data processor 70 can execute calculation processing or the like for obtaining the size (layer thickness, volume, etc.) of the tissue or the distance between predetermined sites. For example, the data processor 70 specifies peak positions of the detection result (interference signal) of the interference light corresponding to the predetermined sites in the eye by analyzing the scan data or the tomographic image, and obtains the intraocular distance based on the distance between the specified peak positions. In some embodiments, the data processor 70 obtains the intraocular distance (distance between layers) based on the number of pixels existing between the two layer regions obtained by performing segmentation processing and a predetermined spacing correction value. The measurement of the intraocular distance is performed along a predetermined direction. The measurement direction of the intraocular distance may be, for example, a direction determined by OCT scan (for example, the traveling direction of the measurement light), or a direction determined based on scan data (for example, the direction orthogonal to the layer). Further, the distance data may be distance distribution data between the two layer regions, a statistic value (for example, average, maximum value, minimum value, median, mode, variance, standard deviation) calculated from this distance distribution data, or distance data between representative points of each layer region. Examples of the intraocular distance, which the data processor 70 can calculate, include an axial length, a corneal thickness, an anterior chamber depth, a crystalline lens thickness, a length of vitreous cavity, a retinal thickness, a choroidal thickness, and the like. Further, the data processor 70 is capable of calculating various parameters representing optical characteristics of the eyeball using the obtained intraocular distance.

In some embodiments, the specifying unit 722 (or the eyeball model building unit 73B) is capable of specifying the shape of the fundus Ef using the built eyeball model. For example, the specifying unit 722 specifies the shape of the fundus Ef by obtaining a difference between a central region of the fundus Ef and the depth position of the peripheral region.

(Peripheral Refractive Power Calculator 73C)

The peripheral refractive power calculator 73C calculates the refractive power of the peripheral region outside the region including the fovea in the fundus Ef. At this time, the peripheral refractive power calculator 73C calculates the refractive power of the peripheral region based on the refractive power of the central region acquired by the refractometry unit 20 and the specified shape of the fundus Ef. The peripheral refractive power calculator 73C is capable of calculating the refractive power of the peripheral region using the parameters of the eyeball model built by the eyeball model building unit 73B.

In some embodiments, the functions of the data processor 70 are realized by one or more processors. In some embodiments, each function of the alignment processor 71, the analyzer 72, and the calculator 73 is realized by a single processor. In some embodiments, the function of each part of the alignment processor 71 is realized by a single processor. In some embodiments, the function of the analyzer 72 is realized by a single processor. In some embodiments, the function of each part of the calculator 73 is realized by a single processor. In some embodiments, at least part of the data processor 70 is provided in the refractometry unit 20 or the OCT unit 30.

(Controller 80)

The controller 80 controls each part of the ophthalmologic apparatus 1. The controller 80 includes a storage unit (now shown), and can store various types of information. Examples of the information stored in the storage unit include a program for controlling each part of the ophthalmologic apparatus 1, information of the subject, information of the subject's eye, measurement data acquired by the measurement unit 10, processing results by the data processor 70, and the like. The functions of the controller 80 is realized by a processor.

The controller 80 is capable of controlling a display device (not shown). Upon receiving control of the controller 80, the display device displays information, as a part of user interface. The display device may be, for example, a liquid crystal display (LCD), or an organic light-emitting diode (OLED) display.

The controller 80 can control the ophthalmologic apparatus 1 in accordance with a signal from an operation device (not shown). The operation device functions as a part of the user interface unit. The operation device may include various types of hardware keys (the joystick, buttons, switches, etc.) provided in the ophthalmologic apparatus 1. Further, the operation device may include various types of peripheral devices (keyboard, mouse, joystick, operation panel, etc.) connected to the ophthalmologic apparatus 1. Further, the operation device may include various kinds of software keys (buttons, icons, menus, etc.) displayed on the touch panel.

(Movement Mechanism 90)

The movement mechanism 90 is a mechanism for moving the head unit in upper and horizontal directions and front-back direction, the head unit housing the optical systems (optical systems of the apparatus) such as the refractometry unit 20, the OCT unit 30, the alignment light projection unit 40, the beam splitters BS1 and BS2, and the like. The movement mechanism 90 can relatively move the measurement unit 10 with respect to the subject's eye E under the control of the controller 80. For example, the movement mechanism 90 is provided with an actuator that generates driving force for moving the head unit and a transmission mechanism that transmits the driving force to the head unit. The actuator is configured by a pulse motor, for example. The transmission mechanism is configured by a combination of gears, a rack and pinion, and the like, for example. The main controller 80 controls the movement mechanism 90 by sending a control signal to the actuator.

The control for the movement mechanism 90 is used for position matching (alignment). For example, the controller 80 obtains a current position of the measurement unit 10 (optical system of the apparatus). The controller 80 receives information representing the content of the movement control of the movement mechanism 90, and obtains the current position of the measurement unit 10. In this case, the controller 80 controls the movement mechanism 90 at a predetermined timing (upon start-up of the apparatus, upon inputting patient information, etc.) to move the measurement unit 10 to a predetermined initial position. Thereafter, the controller 80 records the control content each time the movement mechanism 90 is controlled. Thereby, a history of the control contents can be obtained. As an optical system position obtaining unit, the controller 80 refers to this history, obtains the control contents up to the present time, and determines the current position of the measurement unit 10 based on the control contents.

In some embodiments, each time the controller 80 controls the movement mechanism 90, the controller 80 receives the control content and sequentially obtains the current position of the measurement unit 10. In some embodiments, a position sensor is provided in the ophthalmologic apparatus 1, the position sensor detecting the position of the measurement unit 10. The controller 80 obtains the current position of the measurement unit 10 based on the detection result of the position sensor.

The controller 80 can control the movement mechanism 90 based on the current position obtained as described above and the movement target position determined by the movement target position determining unit 71C. Thereby, the measurement unit 10 can be moved to the movement target position. For example, the controller 80 obtains a difference between the current position and the movement target position. The value of this difference is a vector value having the current position as a start point and the movement target position as an end point, for example. This vector value is a three-dimensional vector value expressed in the xyz coordinate system, for example.

In some embodiments, the control for the movement mechanism 90 is used for tracking. Here, tracking is to move the optical system of the apparatus according to the movement of the subject's eye E. To perform tracking, alignment and focus adjustment are performed in advance. The tracking is a function of maintaining a suitable positional relationship in which alignment and focusing are matched by causing the position of the optical system of the apparatus and the like to follow the eye movement.

The control processor 50 or the data processor 70 is an example of the "ophthalmologic information processing apparatus" according to the embodiments. The OCT unit 30 and the imaging unit 60 or the device (a communication interface, an input/output interface, etc.) for receiving data from the external apparatus (external ophthalmologic apparatus) or a recording medium are (is) an example of the "acquisition unit" according to the embodiments. The OCT unit 30 and the image forming unit 60 are an example of the "OCT unit" according to the embodiments. The shape profile acquired by the layer region specifying unit 721 is an example of the "first shape data" according to the embodiments. The layer region specifying unit 721 is an example of the "tissue specifying unit" according to the embodiments. The shape profile obtained by performing statistical processing by the statistics processor 722B is an example of the "second shape data" according to the embodiments. The specifying unit 722 or the statistics processor 722B is an example of the "specifying part" according to the embodiments.

Operation Example

The operation of the ophthalmologic apparatus 1 according to the present embodiment will be described.

Figure 8:
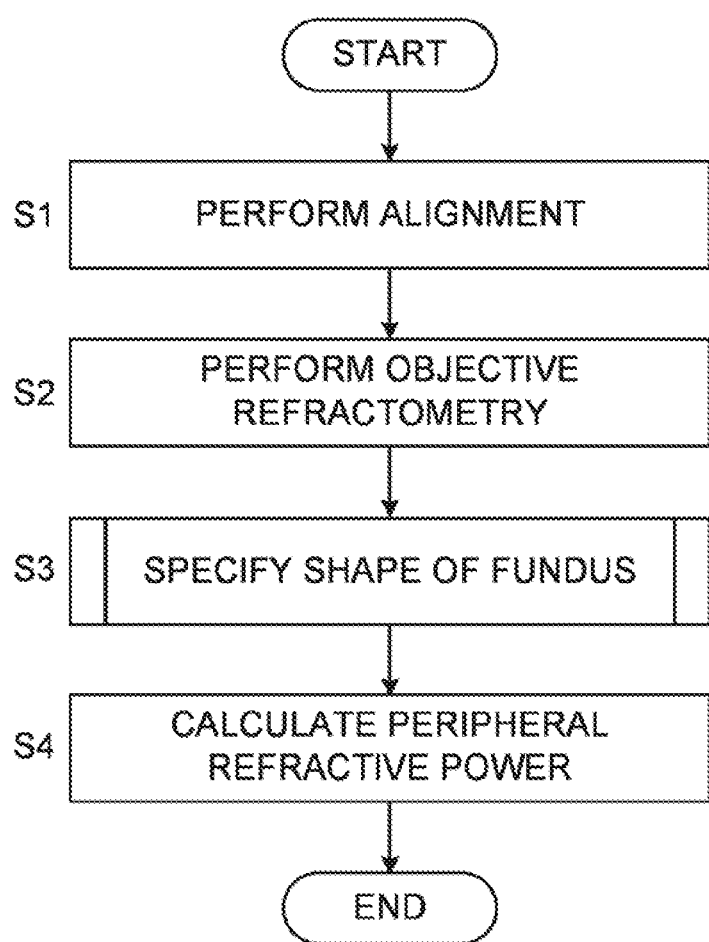
FIG. 8 is a flowchart illustrating an example of the operation of the ophthalmologic apparatus according to the embodiments.
Figure 9:
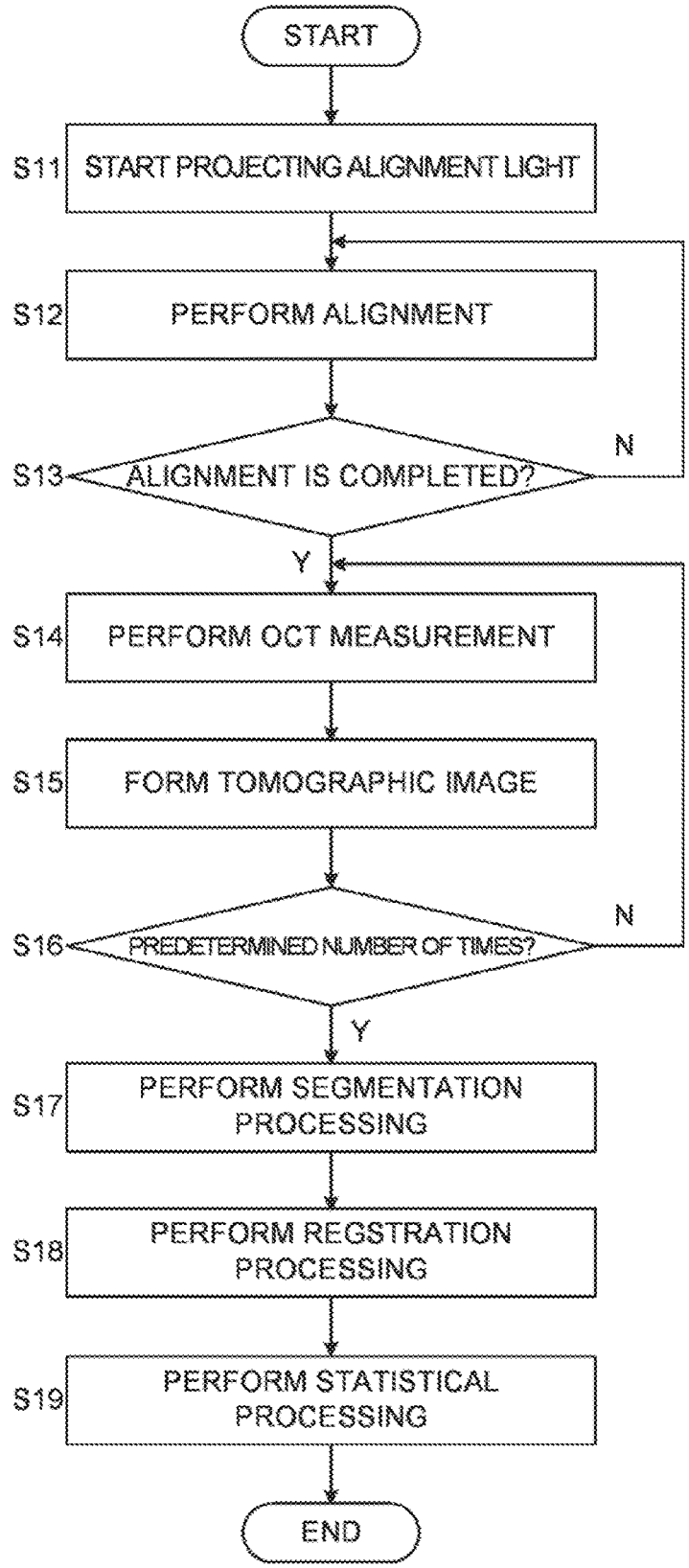
FIG. 9 is a flowchart illustrating an example of the operation of the ophthalmologic apparatus according to the embodiments.

FIGS. 8 and 9 illustrate an example of the operation of the ophthalmologic apparatus 1. FIG. 8 shows a flowchart of an example of the operation of the ophthalmologic apparatus 1. FIG. 9 shows a flowchart of an example of the operation of step S3 in FIG. 8. The storage unit of the controller 80 stores a of computer programs for realizing the processing shown in FIGS. 8 and 9. The controller 80 operates according to the computer programs, and thereby the controller 80 performs the processing shown in FIGS. 8 and 9.

(S1: Perform Alignment)

First, the controller 80 performs alignment.

For example, the controller 80 controls the alignment light projection unit 40 to project the alignment light onto the subject's eye E. At this time, a fixation light flux is projected onto the subject's eye E at a predetermined projection position (for example, a projection position on the measurement optical axis) by a fixation projection system (not shown). For example, the controller 80 specifies a movement amount and a movement direction of the measurement unit 10 from the displacement between the pupil center position and the position of the Purkinje image in the photographic image acquired by the imaging unit 100, and controls the movement mechanism 90 based on the specified movement amount and the specified movement direction to perform position matching of the measurement unit 10 with respect to the subject's eye E. The controller 80 repeatedly executes this processing until a predetermined alignment completion condition is satisfied.

(S2: Perform Objective Refractometry)

Next, the controller 80 controls the fixation projection system (not shown) to project a fixation target on the measurement optical axis of the optical system of the refractometry unit 20 in the fundus Ef (central fixation). After that, the controller 80 controls the refractometry unit 20 to perform objective refractometry in a state in which the fixation target is projected on the measurement optical axis of the optical system of the refractometry unit 20.

The refractive power calculator 73A calculates the refractive power of the central region including the fovea of the subject's eye E by analyzing the ring pattern image formed by the reflected light of the light projected onto the fundus Ef of the subject's eye E.

(S3: Specify Shape of Fundus)

Subsequently, the controller 80 performs the processing for specifying the shape of the fundus Ef of the subject's eye E. In the embodiments, the controller 80 controls the OCT unit 30 to perform OCT measurement (OCT scan) in a state in which the fixation target is projected on the measurement optical axis of the optical system of the refractometry unit 20 (OCT unit 30).

In step S3, the shape data representing the shape of the fundus Ef is acquired as described above. Details of step S3 will be described later.

(S4: Calculate Peripheral Refractive Power)

Subsequently, the controller 80 controls the peripheral refractive power calculator 73C to calculate the refractive power of the peripheral region outside the central region including the fovea obtained in step S2. Therefore, the controller 80 controls the eyeball model building unit 73B to build the eyeball model.

Specifically, the eyeball model building unit 73B obtains Height shape data [pixel] of the predetermined layer region from the data acquired in step S3. The Height data corresponds to a distance in the depth direction from a predetermined reference position in the tomographic image. The eyeball model building unit 73B obtains a distance [mm] of the Height data using pixel spacing correction value [mm/pixel] which is defined by the optical system and is specific to the apparatus. Further, the eyeball model building unit 73B builds the eyeball model using the obtained Height data as fundus shape data.

Figure 10:
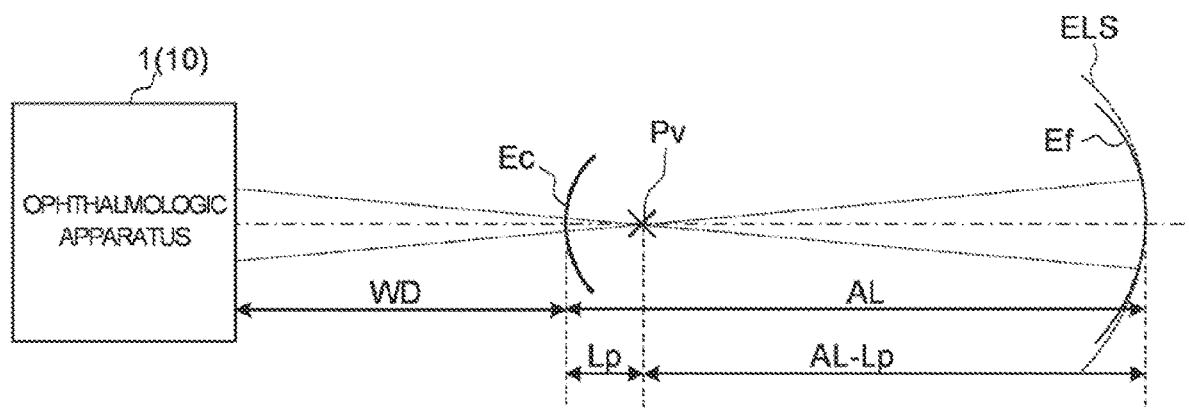
FIG. 10 is a schematic diagram for explaining an operation of the ophthalmologic apparatus according to the embodiments.

FIG. 10 shows a diagram describing the operation of the eyeball model building unit 73B according to the embodiments. FIG. 10 schematically illustrates a part of parameters of the eyeball model.

The eyeball model building unit 73B builds the eyeball model having a predetermined corneal curvature radius (for example, 7.7 mm) and a predetermined axial length (for example, 24.2 mm) using parameters of an eyeball model such as Gullstrand schematic eye.

The eyeball model building unit 73B sets a pivot point Pv, which is specific to the apparatus, between the cornea Ec and the fundus Ef in the eyeball model, as shown in FIG. 10. Typically, a position corresponding to a pupil position disposed at a position optically conjugate with the optical scanner included in the scan system (for example, a position of 3 mm apart on the rear side with respect to the cornea Ec) is set as the pivot point Pv. Equidistant (equal optical path length) positions (ELS) about the pivot point Pv correspond to flat positions in the tomographic image obtained by the OCT measurement.

In the eyeball model, the axial length AL and the distance Lp from the anterior surface (posterior surface) of the cornea to the pivot point Pv are known. Therefore, the distance (AL-Lp) from the pivot point Pv to the fundus Ef is known. When the curvature radius of the fundus Ef is equal to the distance (AL-Lp), the equidistant positions correspond to the flat positions in the tomographic image as described above. Thereby, the eyeball model building unit 73B can specify the shape (for example, curvature radius) of the fundus Ef from the distance [mm] of the obtained Height data.

Therefore, the eyeball model building unit 73B obtains the difference (fundus shape difference data) $\Delta h$ [mm] of the height of the peripheral region with respect to the central region (fovea). The difference $\Delta h$ may be obtained for each A line in the tomographic image, or may be obtained by fitting with an arbitrary function such as a polynomial or an aspheric expression (polynomial including a conic constant).

Next, the peripheral refractive power calculator 73C defines a refractive power of the whole eye system in order to relate the shape of the fundus and the refractive power. In a typical eyeball model (Gullstrand schematic eye (precise schematic eye, accommodation pausing state)), the refractive power of the whole eye system is 58.64 [Diopter]. In the air conversion length, the focal length of the whole eye system is "1000/58.64=17.05" [mm]. Information on unit [mm] obtained using the pixel spacing correction value usually represents the distance in tissue of the living body. Thereby, the focal length of the whole eye system in tissue of the living body can be calculated by multiplying a refractive index. Assuming that the equivalent refractive index of the whole eye system is n=1.38, the focal length ft of the whole eye system in tissue of the living body is "1000/58.64×1.38=23.53" [mm].

The peripheral refractive power calculator 73C calculates the difference $\Delta D$ of the eyeball refractive power at the position of the difference $\Delta h$ of the height of the peripheral region with respect to the central region (fovea) according to expression (1). The difference $\Delta D$ corresponds to the difference in the eyeball refractive power relative to the central region including the fovea.

[Expression 1]

$$\Delta D = \frac{1000}{23.53 - \Delta h} - \frac{1000}{23.53} \quad (1)$$

For example, when $\Delta h=0.1$ [mm] (in tissue), $\Delta D=0.18$ [Diopter].

The peripheral refractive power calculator 73C obtains the refractive power SEp of the peripheral region by applying the difference $\Delta D$ of expression (1) to the equivalent spherical power SE of the central region, as shown in expression (2).

[Expression 2]

$$SEp = SE + \Delta D \quad (2)$$

The peripheral refractive power calculator 73C may obtain the refractive power of the peripheral region in the tomographic image for each A line, or may obtain by fitting with an arbitrary function.

This terminates the operation of the ophthalmologic apparatus 1 (END).

In step S3 in FIG. 8, processing for specifying the shape of the fundus Ef of the subject's eye E is performed as shown in FIG. 9.

(S11: Start Projection Alignment Light)

When the processing of step S3 is started, the controller 80 controls the alignment light projection unit 40 to start projecting the alignment light onto the subject's eye E.

Also in step S11, in the same manner as in step S1, the fixation light flux is projected onto the subject's eye E at the predetermined projection position (for example, the projection position on the measurement optical axis) by the fixation projection system (not shown).

(S12: Perform Alignment)

The controller 80 specifies a movement amount and a movement direction of the measurement unit 10 from the displacement between the pupil center position and the position of the Purkinje image in the photographic image acquired by the imaging unit 100, and controls the movement mechanism 90 based on the specified movement amount and the specified movement direction to perform position matching of the measurement unit 10 with respect to the subject's eye E.

(S13: Alignment is Completed?)

The controller 80 determines whether the predetermined alignment completion condition is satisfied. The alignment completion condition includes that a position of the optical axis of the measurement unit 10 in the x and the y directions coincides with the movement target position in the x and the y directions, and that a distance in the z direction becomes a predetermined working distance. In some embodiments, the working distance is the working distance of the measurement unit 10 (objective lens).

When it is determined that the predetermined alignment completion condition is not satisfied (S13: N), the operation of the ophthalmologic apparatus 1 proceeds to step S12. When it is determined that the predetermined alignment completion condition is satisfied (S13: Y), the operation of the ophthalmologic apparatus 1 proceeds to step S14.

(S14: Perform OCT Measurement)

When it is determined that the predetermined alignment completion condition is satisfied (S13: Y) in step S13, the controller 80 controls the OCT unit 30 to perform OCT measurement by perform OCT scan on a predetermined site in the fundus Ef. Examples of the predetermined site include the fovea, the its vicinity, and the like. Examples of the OCT scan include the radial scan, and the like.

(S15: Form Tomographic Image)

Sequentially, the controller 80 controls the image forming unit 60 to form the tomographic image of the fundus Ef based on the scan data acquired in step S14.

(S16: Predetermined Number of Times?)

Next, the controller 80 determines whether or not the OCT measurement has been performed a predetermined number of times. In some embodiments, the predetermined number of times is two or more. The controller 80 can determine whether or not the OCT measurement has been performed the predetermined number of times, based on an operation mode (measurement mode, scan mode) designated in advance or the content of operation performed on an operation unit (not shown).

When it is determined that the OCT measurement has been performed the predetermined number of times (S16: Y), the operation of the ophthalmologic apparatus 1 proceeds to step S17. When it is determined that the OCT measurement has not been performed the predetermined number of times (S16: N), the operation of the ophthalmologic apparatus 1 proceeds to step S14.

(S17: Perform Segmentation Processing)

When it is determined that the OCT measurement has been performed the predetermined number of times (S16: Y) in step S16, the controller 80 controls the layer region specifying unit 721 to specify the predetermined layer region (for example, retinal pigment epithelium layer) by performing segmentation processing on the tomographic image formed in step S15. The controller 80 controls the layer region specifying unit 721 to perform segmentation processing on each of the plurality of tomographic images acquired for the number of repetitions in steps S14 to S16. Thereby, the plurality of shape data (shape profile, etc.) of the predetermined layer region is obtained.

In some embodiments, after the OCT measurement is repeated the predetermined number of times, the plurality of tomographic images is formed. The segmentation processing is performed on each of the formed plurality of tomographic images. In some embodiments, after the OCT measurement is repeated the predetermined number of times, the formation processing of the tomographic image and the segmentation processing on the tomographic image are repeated the predetermined number of times.

(S18: Perform Registration Processing)

Next, the controller 80 controls the registration processor 722A to perform registration of the plurality of shape profiles obtained in step S17. The registration processor 722A performs registration on the plurality of shape profiles in the depth direction as described above.

(S19: Perform Statistical Processing)

Next, the controller 80 controls the statistics processor 722B to perform statistical processing on the plurality of shape profiles on which registration has been performed in step S18. The statistics processor 722B performs, for example, the averaging processing of the plurality of shape profiles on which registration has been performed in step S18, and outputs the profile obtained by averaging the plurality of shape profiles. In step S4 in FIG. 8, the profile output in step S19 is used as the data representing the shape of the predetermined layer region (for example, retinal pigment epithelium layer) corresponding to the shape of the fundus Ef.

This terminates the processing of step S3 in FIG. 8 (END).

Modification Example

The configuration and the operation of the ophthalmologic apparatus according to the embodiments are not limited to the above embodiments.

First Modification Example

In step S4, the eyeball model building unit 73B may build a new eyeball model by replacing at least one of the measured data (for example, measured values of axial length, cornea shape, anterior chamber depth, curvature of crystalline lens, thickness of crystalline lens) among the parameters of the eyeball model such as the Gullstrand schematic eye. In some embodiments, the measured data is obtained from the external measurement apparatus or the electronic health record system. In some embodiments, the axial length, the anterior chamber depth, the curvature of crystalline lens, and the thickness of crystalline lens are obtained from the scan data acquired by the OCT unit 30.

For example, the peripheral refractive power calculator 73C (or the data processor 70) performs ray tracing processing on a ray incident from the cornea Ec, passing through the pupil, and reaching the fundus Ef, using the built new eyeball model (for example, pupil diameter=φ4). In the ray tracing processing, a position of the object point is set to a position corresponding to a far point obtained from the refractive power (equivalent spherical power SE) in the central region acquired in step S2. The far distance L from the cornea Ec to the position corresponding to the far point is "−1000/SE" [mm].

First, the peripheral refractive power calculator 73C performs the ray tracing processing for the central region. The measured data is applied to the eyeball model as described above. Therefore, even in the central region, the ray may not converge at the fundus Ef. In this case, the peripheral refractive power calculator 73C finely adjusts the parameters of the eyeball model so that the ray converges in the central region (the surface of the fundus Ef is the best image surface).

Next, the peripheral refractive power calculator 73C performs the ray tracing processing for the peripheral region using the eyeball model whose parameters are finely adjusted (that is, rays having incident angles with respect to the measurement optical axis passing through a rotational point of the eye are traced). The peripheral refractive power calculator 73C obtains the distance to the object point such that the rays converge on the fundus Ef in the peripheral region, by performing ray tracing processing while changing the distance to the object point. The obtained distance to the object point corresponds to the far point distance Lp in the peripheral region. The peripheral refractive power calculator 73C can obtain the refractive power SEp [Diopter] of the peripheral region using expression (3).

[Expression 3]

$$SEp = -\frac{1000}{Lp} \quad (3)$$

The peripheral refractive power calculator 73C performs ray tracing processing while changing the incident angle in a predetermined incident angle range, and obtains the refractive power SEp of the peripheral region for each incident angle (angle of view). The refractive power in the peripheral region may be a discrete value for each incident angle or may be fitted with an arbitrary function in the incident angle range.

In the present modification examples, the eyeball model is finely adjusted so that the rays converge at the fundus Ef in the central region. Therefore, the obtained refractive power of the peripheral region corresponds to obtaining a relative refractive power with respect to the central region.

Second Modification Example

In the above embodiments, a tilt angle of the predetermined layer region (for example, retinal pigment epithelium layer, OS-RPE boundary surface) of the fundus with respect to the horizontal direction (a predetermined reference direction) may be specified from the above shape data or the tomographic image, as the shape of the central region of the fundus Ef.

The configuration of the ophthalmologic apparatus according to the second modification example is the same as the configuration of the ophthalmologic apparatus 1 according to the embodiments except that the eyeball model building unit 73B is omitted. Therefore, the explanation thereof is omitted.

In the present modification example, in step S3, the specifying unit 722 (or the peripheral refractive power calculator 73C) calculates a tilt angle θh of the fundus plane for the tomographic image (B scan image) in the horizontal direction and a tilt angle θv of the fundus plane for the B scan image in the vertical direction, using the Height data obtained from the tomographic image acquired in step S15.

The tilt angles θh and θv can be calculated using the same method as a tilt angle g1 as follows.

Figure 11:
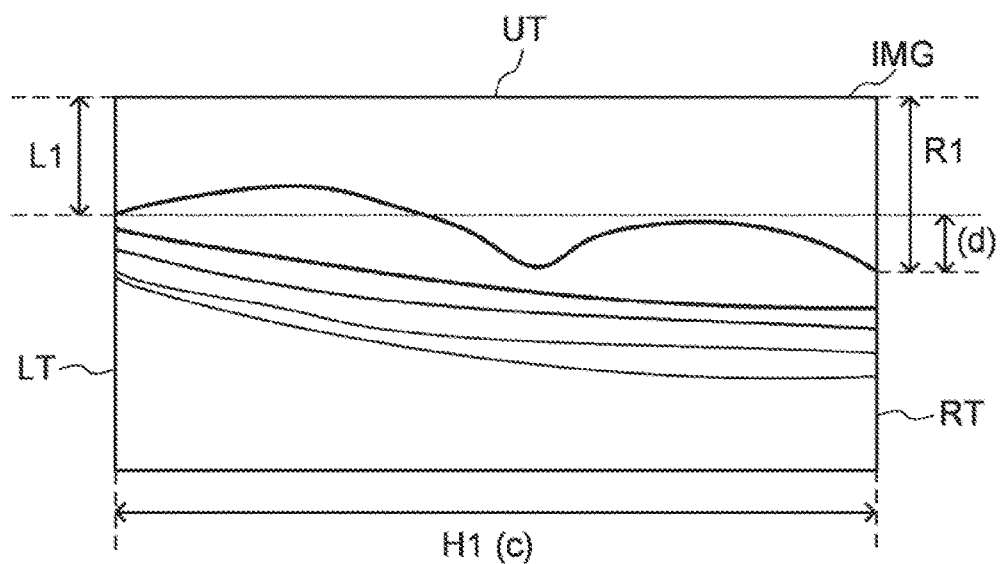
FIG. 11 is a schematic diagram for explaining an operation of the ophthalmologic apparatus according to a modification example of the embodiments.

FIG. 11 schematically shows the tomographic image in the horizontal direction.

In FIG. 11, at the left end LT of the frame of the tomographic image IMG, the distance in the vertical direction from the upper end UT of the frame to the image region of the site corresponding to the predetermined layer region (layer region specified by the layer region specifying unit 721, for example, retinal pigment epithelium layer, OS-RPE boundary surface, or the nerve fiber layer) in the fundus Ef is set as L1. In the same manner, at the right end RT of the frame of the tomographic image IMG, the distance in the vertical direction from the upper end UT of the frame to the image region of the site corresponding to the layer region is set as R1. The distance L1 is obtained using the Height data at the left end LT of the frame. The distance R1 is obtained using the Height data at the right end RT of the frame. The specifying unit 722 obtains a value d corresponding to the actual dimension for the difference (|R1-L1|) in the vertical direction of the image region of the site at the left end LT of the frame and the right end RT of the frame in the tomographic image IMG.

Next, the specifying unit 722 obtains a value c corresponding to the actual dimension for the distance H1 in the horizontal direction of the frame of the tomographic image IMG which corresponds to the OCT measurement range. For example, the value c is specified using the pixel spacing correction value [mm/pixel] for the length of scanning range in the horizontal direction.

The specifying unit 722 obtains an inclination angle g0 [degree] according to expression (4).

[Expression 4]

$$g0 = \arctan\left(\frac{|d|}{c}\right) \quad (4)$$

In some embodiments, the specifying unit 722 obtains the tilt angle of the fundus plane by correcting the inclination angle g0 according to a misalignment amount between the measurement optical axis and the eyeball optical axis.
(In the case that the measurement optical axis and the eyeball optical axis substantially coincide with each other)

When the measurement optical axis and the eyeball optical axis (visual axis) substantially coincide with each other, the specifying unit 722 outputs, as the tilt angle g1 of the fundus plane, the inclination angle g0 of the tomographic image without correcting the inclination angle g0 as shown in expression (5).

[Expression 5]

$$g1 = g0 = \arctan\left(\frac{|d|}{c}\right) \quad (5)$$

(In the case that the eyeball optical axis is shifted with respect to the measurement optical axis)

When the eyeball optical axis is shifted with respect to the measurement optical axis, the specifying unit 722 obtains the tilt angle g1 of the fundus plane by correcting the inclination angle g0 of the tomographic image based on a shift amount.

For example, the specifying unit 722 obtains a correction angle $\varphi 1$ according to a linear expression with the shift amount ds as variable shown in expression (6), and then obtains the tilt angle g1 of the fundus plane by correcting the inclination angle g0 using the obtained correction angle $\varphi 1$ as shown in expression (7). In expression (6), $\alpha 1$ and c1 are constants. For example, $\alpha 1$ and c1 can be obtained using the schematic eye data.

[Expression 6]

$$\varphi 1 = \alpha 1 \times ds + c1 \quad (6)$$

[Expression 7]

$$g1 = g0 - \varphi 1 \quad (7)$$

(In the case that the eyeball optical axis is tilted with respect to the measurement optical axis)

When the eyeball optical axis is tilted with respect to the measurement optical axis, the specifying unit 722 obtains the tilt angle g1 of the fundus plane by correcting the inclination angle g0 of the tomographic image based on a tilt amount.

For example, the specifying unit 722 obtains a correction angle $\varphi 2$ according to a linear expression with the tilt amount dt as variable shown in expression (8), and then obtains the tilt angle g1 of the fundus plane by correcting the inclination angle g0 using the obtained correction angle $\varphi 2$ as shown in expression (9). In expression (8), $\alpha 2$ and c2 are constants. For example, $\alpha 2$ and c2 can be obtained by using the schematic eye data.

[Expression 8]

$$\varphi 2 = \alpha 2 \times dt + c2 \quad (8)$$

[Expression 9]

$$g1 = g0 - \varphi 2 \quad (9)$$

(In the case that the eyeball optical axis is shifted and tilted with respect to the measurement optical axis)

When the eyeball optical axis is shifted and tilted with respect to the measurement optical axis, the specifying unit 722 obtains the tilt angle g1 of the fundus plane by correcting the inclination angle g0 of the B scan image based on the shift amount and the tilt amount.

For example, in a range where the shift amount ds and the tilt amount dt are small, the specifying unit 722 obtains a correction angle $\varphi 3$ according to an expression with the shift amount ds and the tilt amount dt as variables shown in expression (10), and then obtains the tilt angle g1 of the fundus plane by correcting the inclination angle g0 using the obtained correction angle $\varphi 3$ as shown in expression (11). In some embodiments, expression (10) is a combining expression obtained by linearly combined an expression for obtaining the correction angle of the shift amount and an expression for obtaining the correction angle of the tilt amount. In expression (10), $\alpha 3$, $\alpha 4$ and c3 are constants. For example, $\alpha 3$, $\alpha 4$, and c3 can be obtained using the schematic eye data.

[Expression 10]

$$\varphi 3 = \alpha 3 \times ds + \alpha 4 \times dt + c3 \quad (10)$$

[Expression 11]

$$g1 = g0 - \varphi 3 \quad (11)$$

In the present modification example, for horizontal and vertical directions respectively, the refractive power calculator 73A corrects the ring pattern image obtained in step S2 in accordance with the tilt angles θh and θv of the fundus plane specified as described above. The refractive power calculator 73A performs ellipse approximation on the corrected ring pattern image, and obtains the refractive power using the obtained elliptical shape by a known method. The obtained refractive power is calculated as the refractive power of the central region.

For example, a major axis of the ring pattern image is LA, and a minor axis of the ring pattern image is LB, the ring pattern image being acquired when the tilt angle of the fundus plane is 0 degree. When the fundus plane is tilted in the major axis direction and the tilt angle is θ degree, the major axis of the ellipse approximated from the acquired ring pattern image is LA/cos θ, and the minor axis is LB. Therefore, the refractive power calculator 73A can correct the ring pattern image by multiplying cos θ in the major axis direction of the ellipse obtained by approximating the ring pattern image acquired in step S2. The same applies to the case of tilting in the minor axis direction. For example, the refractive power calculator 73A can correct the ring pattern image by obtaining the tilt angle in the major axis direction of the ellipse and the tilt angle in the minor axis direction of the ellipse from each of the tilt angles in the horizontal and vertical directions.

In the same manner as the above embodiments, the peripheral refractive power calculator 73C obtains the refractive power SEp of the peripheral region by applying the difference ΔD of expression (1) to the equivalent spherical power SE of the central region, as shown in expression (2).

Third Modification Example

In the above embodiments or the modification example thereof, the case has been described where the statistical processing is performed after registration of the plurality of shape profiles acquired by performing segmentation processing on the tomographic image. However, the configuration of the ophthalmologic apparatus 1 according to the embodiments is not limited to this. For example, the statistical processing may be performed on the plurality of shape profiles obtained by performing segmentation processing on each of the plurality of tomographic images on which registration has been performed, after registration of the plurality of tomographic images is performed.

In the following, the ophthalmologic apparatus according to the third modification example will be described focusing on differences from the ophthalmologic apparatus 1 according to the embodiments.

In the third modification example, the registration processor 722A performs registration (position matching) of the plurality of tomographic images obtained by the image forming unit 60. The registration processor 722A performs registration on the plurality of tomographic images in the xy directions and the z direction.

In some embodiments, the registration processor 722A obtains a shift amount based on a correlation value of the plurality of tomographic images, and performs registration of the plurality of tomographic images based on the obtained shift amount.

For example, the registration processor 722A calculates the correlation value of the obtained plurality of tomographic images using a known correlation function. The registration processor 722A changes the shift amount of at least one of the plurality of tomographic images to calculate the correlation value again. The registration processor 722A determines whether to update the shift amount to calculate a new correlation value based on the comparison result of an original correlation value and the correlation value newly calculated. The registration processor 722A repeats the calculation of the correlation value and the comparison to obtain the shift amount (including shift direction) at which the correlation value becomes maximum, and performs registration of at least one of the plurality of tomographic images based on the obtained shift amount.

In some embodiments, the registration processor 722A extracts characteristic parts from the acquired plurality of tomographic images, and performs registration of the plurality of tomographic images with reference to the extracted characteristic parts.

For example, the registration processor 722A extracts a characteristic part from each of the acquired plurality of tomographic images. In some embodiments, a characteristic shaped part of the tomographic image is specified as the characteristic part. In some embodiments, the characteristic part of the tomographic image, the characteristic part corresponding to the characteristic region of the subject's eye E specified by analyzing the front image (fundus image) of the subject's eye E, is specified. Examples of the characteristic shaped parts include a characteristic site (fovea, macular region, optic disc) of the subject's eye, a lesion of the subject's eye, and the like. The registration processor 722A performs registration on at least one of the plurality of tomographic images so that both of the positions of the extracted characteristic part and the orientations of the extracted characteristic part coincide each other.

In the present modification example, the layer region specifying unit 721 performs segmentation processing on each of the plurality of tomographic images on which registration has been performed by the registration processor 722A. The statistics processor 722B performs statistical processing on the plurality of shape profiles obtained by performing segmentation processing by the layer region specifying unit 721.

Figure 12:
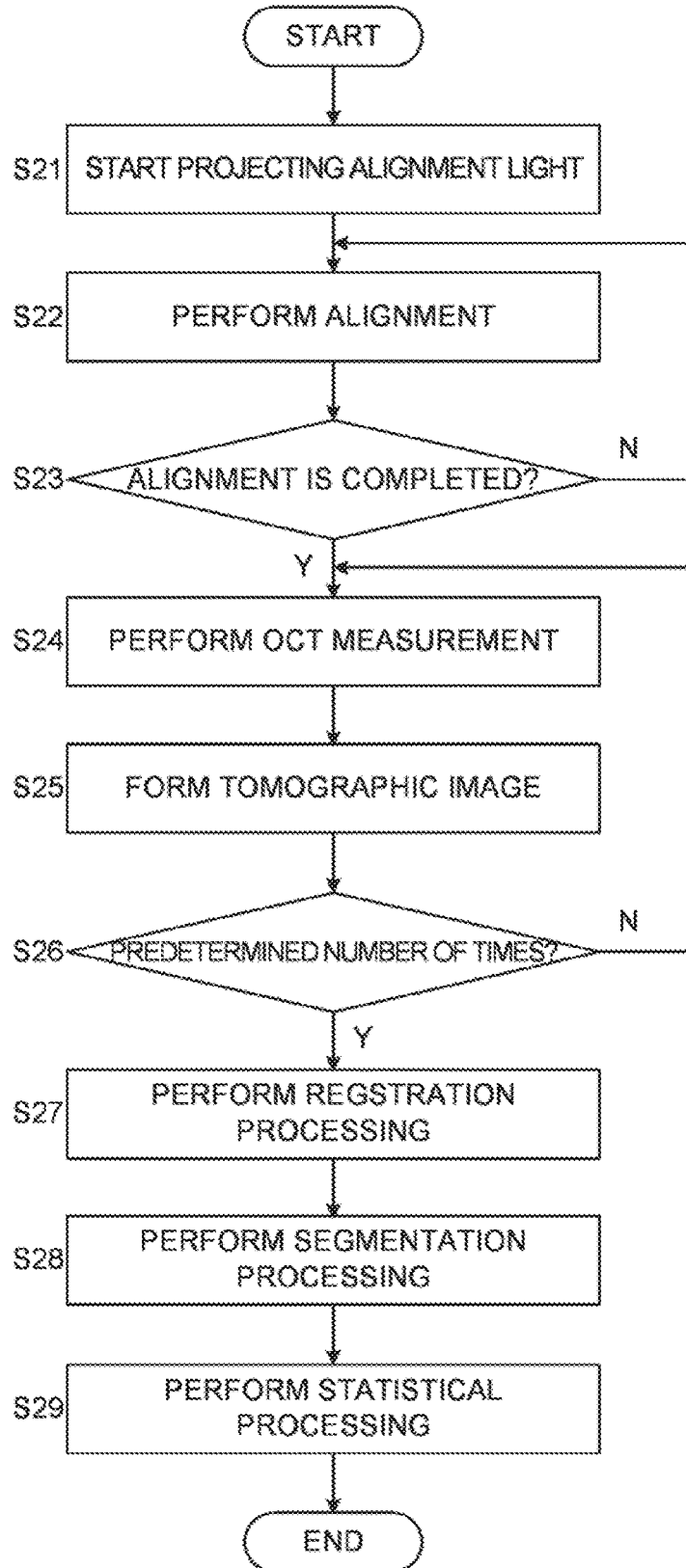
FIG. 12 is a flowchart illustrating an example of the operation of the ophthalmologic apparatus according to a modification example of the embodiments.

The ophthalmologic apparatus according to the third modification example is capable of operating as shown in FIG. 12. The ophthalmologic apparatus according to the third modification example is capable of operating as follow, in step S3 of FIG. 8.

FIG. 12 shows an example of the operation of the ophthalmologic apparatus 1 according to the third modification example. FIG. 12 shows a flowchart of an example of the operation of the ophthalmologic apparatus 1. The storage unit of the controller 80 stores a of computer programs for realizing the processing shown in FIG. 12. The controller 80 operates according to the computer programs, and thereby the controller 80 performs the processing shown in FIG. 12.

That is, in the present modification example, in step S3 in FIG. 9, processing for specifying the shape of the fundus Ef of the subject's eye E is performed as shown in FIG. 12.

(S21: Start Projection Alignment Light)

When the processing of step S3 is started, the controller 80 controls the alignment light projection unit 40 to start projecting the alignment light onto the subject's eye E in the same manner as in step S11.

(S22: Perform Alignment)

The controller 80 controls the movement mechanism 90 to perform position matching of the measurement unit 10 with respect to the subject's eye E in the same manner as in step S12.

(S23: Alignment is Completed?)

The controller 80 determines whether the predetermined alignment completion condition is satisfied in the same manner as in step S13.

When it is determined that the predetermined alignment completion condition is not satisfied (S23: N), the operation of the ophthalmologic apparatus according to the present modification example proceeds to step S22. When it is determined that the predetermined alignment completion condition is satisfied (S23: Y), the operation of the ophthalmologic apparatus according to the present modification example proceeds to step S24.

(S24: Perform OCT Measurement)

When it is determined that the predetermined alignment completion condition is satisfied (S23: Y), the controller 80 controls the OCT unit 30 to perform OCT scan on a predetermined site in the fundus Ef to perform OCT measurement in the same manner as in step S14.

(S25: Form Tomographic Image)

Sequentially, the controller 80 controls the image forming unit 60 to form the tomographic image of the subject's eye E based on the scan data obtained in step S24, in the same manner as step S15.

(S26: Predetermined Number of Times?)

Next, the controller 80 determines whether or not the OCT measurement has been performed a predetermined number of times, in the same manner as step S16.

When it is determined that the OCT measurement has been performed the predetermined number of times (S26: Y), the operation of the ophthalmologic apparatus 1 proceeds to step S27. When it is determined that the OCT measurement has not been performed the predetermined number of times (S26: N), the operation of the ophthalmologic apparatus 1 proceeds to step S24.

(S27: Perform Registration Processing)

When it is determined that the OCT measurement has been performed the predetermined number of times (S26: Y) in step S26, the controller 80 controls the registration processor 722A to perform registration of the plurality of tomographic images formed in step S25. The registration processor 722A performs registration of the plurality of tomographic images as described above.

(S28: Perform Segmentation Processing)

Next, the controller 80 controls the layer region specifying unit 721 to specify the predetermined layer region (for example, retinal pigment epithelium layer) by performing segmentation processing on the tomographic image on which registration has been performed in step S27. The controller 80 controls the layer region specifying unit 721 to perform segmentation processing on each of the plurality of tomographic images acquired for the number of repetitions in steps S24 to S26. Thereby, the plurality of shape data (shape profiles, etc.) of the predetermined layer region is obtained.

(S29: Perform Statistical Processing)

Next, the controller 80 controls the statistics processor 722B to perform statistical processing on the plurality of shape profiles obtained in step S28, in the same manner as in step S19. The statistics processor 722B performs, for example, the averaging processing of the plurality of shape profiles obtained in step S28, and outputs the profile obtained by averaging the plurality of shape profiles. In step S4 in FIG. 8, the profile output in step S29 is used as the data representing the shape of the predetermined layer region (for example, retinal pigment epithelium layer) corresponding to the shape of the fundus Ef.

This terminates the processing of step S3 in FIG. 8 (END).

Fourth Modification

In the above embodiments or the modification example thereof, the case where the statistical processing is performed on the plurality of shape profiles obtained by performing segmentation processing by the layer region specifying unit 721 has been mainly described. However, the configuration according to the embodiments is not limited to this. For example, parameters corresponding to the shape profiles may be obtained for each of the plurality of shape profiles obtained by performing segmentation processing by the layer region specifying unit 721. And the statistical processing may be performed on the obtained plurality of parameters, and the shape profiles representing the true shape of the predetermined layer region may be obtained from the parameters after the statistical processing.

In the following, the ophthalmologic apparatus according to the fourth modification example will be described focusing on differences from the ophthalmologic apparatus 1 according to the embodiments.

In the fourth modification example, the statistics processor 722B performs statistical processing on the plurality of shape profiles on which registration processing has been performed by the registration processor 722A, and outputs the shape profile after statistical processing, in the same manner as the above embodiments. At this time, the statistics processor 722B obtains shape parameters for each of the plurality of shape profiles on which registration processing has been performed by the registration processor 722A, and performs statistical processing on the obtained plurality of shape parameters, and obtains the shape profiles representing the true shape of the predetermined layer region from the shape parameters after statistical processing.

Examples of the shape parameter include a coefficient of a polynomial obtained by polynomial approximation of the shape of a predetermined layer region, a curvature and a central coordinate position when the shape of the predetermined layer region is represented by a sphere (or circle), a coefficient when the shape of the predetermined layer region is represented by a curve of second order or high order, and the like.

Examples of the statistical processing include averaging processing, median calculation processing, mode calculation processing, maximum likelihood value calculation processing, maximum calculation processing, minimum calculation processing, and the like. The statistical processing may include weighting processing for obtaining a statistical value by weighting in accordance with the image quality of the tomographic image, measurement accuracy, amount of alignment error, or displacement amount after registration of the shape profile. In some embodiments, the statistical processing is performed excluding the shape parameters that deviate by a predetermined threshold or more from the standard deviation when the shape parameter is removed.

For example, in case of polynomial approximation of the shape of the predetermined layer region, the statistics processor 722B obtains a polynomial by performing polynomial approximation using a known method for each of the plurality of shape profiles on which registration processing by the registration processor 722A has been performed, and specifies the coefficient of the polynomial each of the plurality of shape profiles. For example, the coefficient of the polynomial obtained by polynomial approximation of the shape profile obtained by the first OCT measurement is (a1, a2, a3, a4), the coefficient of the polynomial obtained by polynomial approximation of the shape profile obtained by the second OCT measurement is (b1, b2, b3, b4), the coefficient of the polynomial obtained by polynomial approximation of the shape profile obtained by the third OCT measurement is (c1, c2, c3, c4), and the coefficient of the polynomial obtained by polynomial approximation of the shape profile obtained by the fourth OCT measurement is (d1, d2, d3, d4). The statistics processor 722B obtains the true shape parameters (T1, T2, T3, T4) by performing, for example, averaging processing on the coefficients (a1, a2, a3, a4) to (d1, d2, d3, d4) of polynomials obtained by approximating each of the above plurality of shape profiles. The statistics processor 722B obtains a polynomial representing the true shape of the predetermined layer region from the obtained true shape parameters (T1, T2, T3, T4), and outputs the shape profile representing the true shape.

Also in the fourth modification example, the calculator 73 can calculate a refractive power of the peripheral region of the region including the fovea of the subject's eye E using the shape profile output by the statistics processor 722B as the shape of the fundus Ef, in the same manner as the embodiments.

[Effects]

The ophthalmologic apparatus and the method of controlling the ophthalmologic apparatus according to the embodiments are explained.

An ophthalmologic information processing apparatus (control processor 50, or data processor 70) according to some embodiments includes an acquisition unit (OCT unit 30 and image forming unit 60, or a device ((communication interface, input/output interface, etc.) that receives data from an external apparatus (external ophthalmologic apparatus) or a recording medium), a tissue specifying unit (layer region specifying unit 721), and a specifying unit (722). The acquisition unit is configured to acquire a tomographic image of a subject's eye (E). The tissue specifying unit is configured to acquire first shape data (shape profile) representing shape of a tissue of the subject's eye by performing segmentation processing on each of a plurality of tomographic images acquired by the acquisition unit. The specifying unit is configured to obtain second shape data (shape profile) representing shape of the tissue based on the plurality of first shape data acquired by the tissue specifying unit.

According to such a configuration, the second shape data is obtained from the plurality of first shape data. Thereby, the influence of the displacement between the subject's eye and the optical system for measuring the shape of the tissue can be reduced, and the shape of the tissue of the subject's eye can be specified with high reproducibility and high accuracy.

In some embodiments, the specifying unit obtains the second shape data by performing statistical processing on the plurality of first shape data.

According to such a configuration, the second shape data is obtained by performing statistical processing on the plurality of first shape data. Thereby, the influence of the displacement between the subject's eye and the optical system for measuring the shape of the tissue can be reduced with simple processing, and the shape of the tissue of the subject's eye can be specified with high reproducibility and high accuracy.

In some embodiments, the specifying unit obtains the second shape data based on a maximum likelihood value obtained by performing statistical processing on the plurality of first shape data.

According to such a configuration, the maximum likelihood value is obtained in the statistical processing. Thereby, the shape of the tissue of the subject's eye can be specified with simple processing, high reproducibility and high accuracy.

In some embodiments, the statistical processing includes averaging processing.

According to such a configuration, the average processing is used as the statistical processing. Thereby, the shape of the tissue of the subject's eye can be specified with simple processing, high reproducibility and high accuracy.

Some embodiments further include a registration processor (722A) that performs registration of the plurality of first shape data acquired by the tissue specifying unit, wherein the specifying unit obtains the second shape data based on the plurality of first shape data on which registration has been performed by the registration processor.

According to such a configuration, registration of the plurality of first shape data is performed, and the second shape data is obtained from the first shape data on which registration has been performed. Thereby, regardless of variations in the first shape data based on the displacement between the subject's eye and the optical system for measuring the shape of the tissue, the shape of the tissue of the subject's eye can be specified with high reproducibility and high accuracy.

In some embodiments, the registration processor obtains a shift amount based on a correlation value of the plurality of tomographic images, and performs registration of the plurality of first shape data based on the obtained shift amount.

According to such a configuration, the registration of the plurality of first shape data is performed based on the correlation value between the tomographic images. Thereby, the shape of the tissue of the subject's eye can be specified with simple processing, high reproducibility and high accuracy.

In some embodiments, the registration processor performs registration of the plurality of first shape data based on constant terms of polynomials obtained by performing polynomial approximation on each of the plurality of first shape data.

According to such a configuration, the registration of the plurality of first shape data is performed using the constant obtained by performing polynomial approximation on each of shape data. Thereby, the shape of the tissue of the subject's eye can be specified with simple processing, high reproducibility and high accuracy.

In some embodiments, the registration processor extracts each characteristic parts of the plurality of first shape data, and performs registration of the plurality of first shape data with reference to the extracted characteristic parts.

According to such a configuration, the registration of the plurality of first shape data is performed based on the characteristic part of the shape data. Thereby, the shape of the tissue of the subject's eye can be specified with simple processing, high reproducibility and high accuracy.

Some embodiments further include a registration processor (722A) that performs registration of the plurality of tomographic images, wherein the tissue specifying unit performs segmentation processing on each of the plurality of tomographic images on which registration has been performed by the registration processor.

According to such a configuration, registration of the plurality of tomographic images is performed, and the plurality of first shape data is obtained by performing segmentation processing on each of the plurality of tomographic images on which registration has been performed. Thereby, regardless of variations in the first shape data based on the displacement between the subject's eye and the optical system for measuring the shape of the tissue, the shape of the tissue of the subject's eye can be specified with high reproducibility and high accuracy.

In some embodiments, the registration processor obtains a shift amount based on a correlation value of the plurality of tomographic images, and performs registration of the plurality of tomographic images based on the obtained shift amount.

According to such a configuration, the registration of the plurality of tomographic images is performed based on the correlation value between the tomographic images. Thereby, the shape of the tissue of the subject's eye can be specified with simple processing, high reproducibility and high accuracy.

In some embodiments, the tissue includes a predetermined layer region (for example, retinal pigment epithelium layer) in a fundus (Ef).

According to such a configuration, the shape of the fundus can be specified with high reproducibility and high accuracy, without being affected by the displacement between the subject's eye and the OCT unit.

Some embodiments further include a calculator (peripheral refractive power calculator 73C) that calculates a refractive power of a peripheral region of a region including a fovea of the subject's eye based on a refractive power obtained by objectively measuring the subject's eye and parameter representing optical characteristics of the subject's eye corresponding to the shape of the tissue on the basis of the second shape data acquired by the specifying unit.

According such a configuration, in accordance with the shape of the fundus of the subject's eye, the refractive power of the peripheral region of the region including the fovea can be obtained with high accuracy.

In some embodiments, the shape of the tissue includes a tilt angle of the tissue with respect to a predetermined reference direction.

According to such a configuration, in accordance with the tilt angle of the predetermined layer region in the fundus with respect to the predetermined reference direction, the refractive power of the peripheral region of the region including the fovea can be obtained with high accuracy.

An ophthalmologic apparatus (1) according to some embodiments includes the ophthalmologic information processing apparatus described in any of the above, wherein the acquisition unit includes an OCT unit (30) configured to acquire the tomographic image of the subject's eye by performing optical coherence tomography.

According to such a configuration, the ophthalmologic apparatus, which is capable of reducing the influence of the displacement between the subject's eye and the optical system for measuring the shape of the tissue, and of specifying the shape of the tissue of the subject's eye with high reproducibility and high accuracy, can be provided.

An ophthalmologic information processing method includes a tomographic image acquisition step, a tissue specifying step, and a specifying step. The tomographic image acquisition step acquires a tomographic image of a subject's eye. The tissue specifying step acquires first shape data representing shape of a tissue of the subject's eye by performing segmentation processing on each of a plurality of tomographic images acquired in the tomographic image acquisition step. The specifying step obtains second shape data representing shape of the tissue based on the plurality of first shape data acquired in the tissue specifying step.

According to such a method, the second shape data is obtained from the plurality of first shape data. Thereby, the influence of the displacement between the subject's eye and the optical system for measuring the shape of the tissue can be reduced, and the shape of the tissue of the subject's eye can be specified with high reproducibility and high accuracy.

In some embodiments, the specifying step obtains the second shape data by performing statistical processing on the plurality of first shape data.

According to such a method, the second shape data is obtained by performing statistical processing on the plurality of first shape data. Thereby, the influence of the displacement between the subject's eye and the optical system for measuring the shape of the tissue can be reduced with simple processing, and the shape of the tissue of the subject's eye can be specified with high reproducibility and high accuracy.

In some embodiments, the specifying step obtains the second shape data based on a maximum likelihood value obtained by performing statistical processing on the plurality of first shape data.

According to such a method, the maximum likelihood value is obtained in the statistical processing. Thereby, the shape of the tissue of the subject's eye can be specified with simple processing, high reproducibility and high accuracy.

In some embodiments, the statistical processing includes averaging processing.

According to such a method, the average processing is used as the statistical processing. Thereby, the shape of the tissue of the subject's eye can be specified with simple processing, high reproducibility and high accuracy.

Some embodiments further include a registration processing step that performs registration of the plurality of first shape data acquired in the tissue specifying step, wherein the specifying step obtains the second shape data based on the plurality of first shape data on which registration has been performed in the registration processing step.

According to such a method, registration of the plurality of first shape data is performed, and the second shape data is obtained from the first shape data on which registration has been performed. Thereby, regardless of variations in the first shape data based on the displacement between the subject's eye and the optical system for measuring the shape of the tissue, the shape of the tissue of the subject's eye can be specified with high reproducibility and high accuracy.

Some embodiments further include a registration processing step that performs registration of the plurality of tomographic images, wherein the tissue specifying step performs segmentation processing on the plurality of tomographic images on which registration has been performed in the registration processing step.

According to such a method, registration of the plurality of tomographic images is performed, and the plurality of first shape data is obtained by performing segmentation processing on each of the plurality of tomographic images on which registration has been performed. Thereby, regardless of variations in the first shape data based on the displacement between the subject's eye and the optical system for measuring the shape of the tissue, the shape of the tissue of the subject's eye can be specified with high reproducibility and high accuracy.

In some embodiments, the tissue includes a predetermined layer region (for example, retinal pigment epithelium layer) in a fundus (Ef).

According to such a method, the shape of the fundus can be specified with high reproducibility and high accuracy, without being affected by the displacement between the subject's eye and the OCT unit.

Some embodiments further include a calculation step that calculates a refractive power of a peripheral region of a region including a fovea of the subject's eye based on a refractive power obtained by objectively measuring the subject's eye and parameter representing optical characteristics of the subject's eye corresponding to the shape of the tissue on the basis of the second shape data acquired in the specifying step.

According to such a method, in accordance with the shape of the fundus of the subject's eye, the refractive power of the peripheral region of the region including the fovea can be obtained with high accuracy.

A program according to some embodiments causes the computer to execute each step of the ophthalmologic information processing method described in any of the above.

According to such a program, the second shape data is obtained from the plurality of first shape data. Thereby, the program, which is capable of reducing the influence of the displacement between the subject's eye and the optical system for measuring the shape of the tissue, and of specifying the shape of the tissue of the subject's eye with high reproducibility and high accuracy, can be provided.

<Others>

The above-described embodiments are merely examples for carrying out the present invention. Those who intend to implement the present invention can apply any modification, omission, addition, or the like within the scope of the gist of the present invention.

In some embodiments, a program for causing a computer to execute not only the ophthalmologic information processing method described above but also a method of controlling the ophthalmologic apparatus is provided. Such a program can be stored in any kind of recording medium that can be read by the computer. Examples of the recording medium include a semiconductor memory, an optical disk, a magneto-optical disk (CD-ROM, DVD-RAM, DVD-ROM, MO, etc.), a magnetic storage medium (hard disk, floppy (registered trade mark) disk, ZIP, etc.), and the like. The computer program may be transmitted and received through a network such as the Internet, LAN, etc.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An ophthalmologic information processing apparatus comprising:
    an acquisition unit configured to acquire a tomographic image of a subject's eye:
    a tissue specifying unit configured to acquire first shape data representing shape of a tissue of the subject's eye by performing segmentation processing on each of a plurality of tomographic images acquired by the acquisition unit; and
    a specifying unit configured to obtain second shape data representing shape of the tissue based on a plurality of first shape data acquired by the tissue specifying unit, wherein
    the first shape data includes a shape profile representing a change in shape in a predetermined one-dimensional direction, a predetermined two-dimensional direction, or a predetermined three-dimensional direction.

2. The ophthalmologic information processing apparatus of claim 1, wherein
    the specifying unit obtains the second shape data by performing statistical processing on the plurality of first shape data on which registration has been performed by a registration processor to obtain a statistical value for each scan position of an OCT scan in the plurality of first shape data.

3. The ophthalmologic information processing apparatus of claim 2, wherein the statistical processing includes a median calculation processing.

4. The ophthalmologic information processing apparatus of claim 2, wherein the statistical processing includes a mode calculation processing.

5. The ophthalmologic information processing apparatus of claim 2, wherein the statistical processing includes a maximum likelihood value calculation processing.

6. The ophthalmologic information processing apparatus of claim 1, wherein
    the specifying unit obtains the second shape data based on a maximum likelihood value obtained by performing statistical processing on the plurality of first shape data.

7. The ophthalmologic information processing apparatus of claim 6, wherein
    the statistical processing includes averaging processing.

8. The ophthalmologic information processing apparatus of claim 1, further comprising
    a registration processor that performs registration of the plurality of first shape data acquired by the tissue specifying unit, wherein
    the specifying unit obtains the second shape data based on the plurality of first shape data on which registration has been performed by the registration processor.

9. The ophthalmologic information processing apparatus of claim 8, wherein
    the registration processor obtains a shift amount based on a correlation value of the plurality of tomographic images, and performs registration of the plurality of first shape data based on the obtained shift amount.

10. The ophthalmologic information processing apparatus of claim 8, wherein
    the registration processor performs registration of the plurality of first shape data based on constant terms of polynomials obtained by performing polynomial approximation on each of the plurality of first shape data.

11. The ophthalmologic information processing apparatus of claim 8, wherein
    the registration processor extracts each characteristic parts of the plurality of first shape data, and performs registration of the plurality of first shape data with reference to the extracted characteristic parts.

12. The ophthalmologic information processing apparatus of claim 1, wherein
    the tissue includes a predetermined layer region in a fundus.

13. The ophthalmologic information processing apparatus of claim 12, further comprising
    a calculator that calculates a refractive power of a peripheral region of a region including a fovea of the subject's eye based on a refractive power obtained by objectively measuring the subject's eye and parameter representing optical characteristics of the subject's eye corresponding to the shape of the tissue on the basis of the second shape data acquired by the specifying unit.

14. The ophthalmologic information processing apparatus of claim 13, wherein
    the shape of the tissue includes a tilt angle of the tissue with respect to a predetermined reference direction.

15. An ophthalmologic apparatus comprising
    the ophthalmologic information processing apparatus of claim 1, wherein
    the acquisition unit includes an OCT unit configured to acquire the tomographic image of the subject's eye by performing optical coherence tomography.

16. The ophthalmologic information processing apparatus of claim 1, wherein the plurality of shape data have different alignment conditions and scan patterns.

17. The ophthalmologic information processing apparatus of claim 1, wherein the tomographic image of the subject's eye is acquired by performing an OCT scan.

18. An ophthalmologic information processing apparatus comprising:
    an acquisition unit configured to acquire a tomographic image of a subject's eye;
    a tissue specifying unit configured to acquire first shape data representing shape of a tissue of the subject's eye by performing segmentation processing on each of a plurality of tomographic images acquired by the acquisition unit;
    a specifying unit configured to obtain second shape data representing shape of the tissue based on a plurality of first shape data acquired by the tissue specifying unit;
    a registration processor that performs registration of the plurality of tomographic images, wherein the tissue specifying unit performs segmentation processing on each of the plurality of tomographic images on which registration has been performed by the registration processor, and the first shape data includes a shape profile representing a change in shape in a predetermined one-dimensional direction, a predetermined two-dimensional direction, or a predetermined three-dimensional direction.

19. The ophthalmologic information processing apparatus of claim 18, wherein the registration processor obtains a shift amount based on a correlation value of the plurality of tomographic images, and performs registration of the plurality of tomographic images based on the obtained shift amount.

20. The ophthalmologic information processing apparatus of claim 18, wherein the tomographic: age of the subject's eye is acquired by performing an OCT scan.

21. The ophthalmologic information processing apparatus of claim 18, wherein the specifying unit obtains the second shape data by performing statistical processing on the plurality of first shape data to obtain a statistical value for each scan position of the OCT scan in the plurality of first shape data.

22. An ophthalmologic information processing method comprising:

a tomographic image acquisition step that acquires a tomographic image of a subject's eye;

a tissue specifying step that acquires first shape data representing shape of a tissue of the subject's eye by performing segmentation processing on each of a plurality of tomographic images acquired in the tomographic image acquisition step;

a specifying step that obtains second shape data representing shape of the tissue based on the plurality of first shape data acquired in the tissue specifying step, wherein the first shape data including a shape profile representing a change in shape in a predetermined one-dimensional direction, a predetermined two-dimensional direction, or a predetermined three-dimensional direction.

23. The ophthalmologic information processing method of claim 22, wherein the specifying step obtains the second shape data by performing statistical processing on the plurality of first shape data.

24. The ophthalmologic information processing method of claim 22, further comprising a registration processing step that performs registration of the plurality of first shape data acquired in the tissue specifying step, wherein the specifying step obtains the second shape data by performing statistical processing on the plurality of first shape data based on the plurality of first shape data on which registration has been performed in the registration processing step to obtain a statistical value for each scan position of the OCT scan in the plurality of first shape data.

25. The ophthalmologic information processing method of claim 22, wherein the tissue includes a predetermined layer region in a fundus.

26. The ophthalmologic information processing method of claim 25, further comprising a calculation step that calculates a refractive power of a peripheral region of a region including a fovea of the subject's eye based on a refractive power obtained by objectively measuring the subject's eye and parameter representing optical characteristics of the subject's eye corresponding to the shape of the tissue on the basis of the second shape data acquired in the specifying step.

27. The ophthalmologic information processing method of claim 22, further comprising acquiring the tomographic image of the subject's eye by performing an OCT scan.

28. An ophthalmologic information processing method comprising:

a tomographic image acquisition step that acquires a tomographic image of a subject's eye;

a tissue specifying step that acquires first shape data representing shape of a tissue of the subject's eye by performing segmentation processing on each of a plurality of tomographic images acquired in the tomographic image acquisition step;

a specifying step that obtains second shape data representing shape of the tissue based on the plurality of first shape data acquired in the tissue specifying step a registration processing step that performs registration of the plurality of tomographic images, wherein the tissue specifying step performs segmentation processing on the plurality of tomographic images on which registration has been performed in the registration processing step, and the first shape data includes a shape profile representing a change in shape in a predetermined one-dimensional direction, a predetermined two-dimensional direction, or a predetermined three-dimensional direction.

* * * * *